US010828250B2

(12) United States Patent
Davis

(10) Patent No.: US 10,828,250 B2
(45) Date of Patent: Nov. 10, 2020

(54) TOPICAL FORMULATION

(71) Applicant: Adrian Davis, Dorking (GB)

(72) Inventor: Adrian Davis, Dorking (GB)

(73) Assignee: LIMEWAY PHARMA DESIGN LIMITED, Surrey (GB)

( * ) Notice: Subject to any disclaimer, the term of this patent is extended or adjusted under 35 U.S.C. 154(b) by 0 days.

(21) Appl. No.: 15/555,469

(22) PCT Filed: Mar. 2, 2016

(86) PCT No.: PCT/GB2016/050545
§ 371 (c)(1),
(2) Date: Sep. 1, 2017

(87) PCT Pub. No.: WO2016/139471
PCT Pub. Date: Sep. 9, 2016

(65) Prior Publication Data
US 2018/0028438 A1 Feb. 1, 2018

(30) Foreign Application Priority Data
Mar. 3, 2015 (GB) .................................... 1503590

(51) Int. Cl.
| | |
|---|---|
| A61K 9/00 | (2006.01) |
| A61K 47/34 | (2017.01) |
| A61K 47/10 | (2017.01) |
| A61K 47/12 | (2006.01) |
| A61K 8/891 | (2006.01) |
| A61K 47/24 | (2006.01) |
| A61K 31/203 | (2006.01) |
| A61K 8/894 | (2006.01) |
| A61K 8/36 | (2006.01) |
| A61K 8/34 | (2006.01) |
| A61Q 19/08 | (2006.01) |
| A61Q 7/00 | (2006.01) |
| A61K 8/898 | (2006.01) |
| A61K 31/232 | (2006.01) |
| A61K 31/192 | (2006.01) |
| A61K 31/4196 | (2006.01) |
| A61K 31/07 | (2006.01) |
| A61Q 19/00 | (2006.01) |

(52) U.S. Cl.
CPC ............ *A61K 9/0014* (2013.01); *A61K 8/342* (2013.01); *A61K 8/345* (2013.01); *A61K 8/361* (2013.01); *A61K 8/891* (2013.01); *A61K 8/894* (2013.01); *A61K 8/898* (2013.01); *A61K 31/07* (2013.01); *A61K 31/192* (2013.01); *A61K 31/203* (2013.01); *A61K 31/232* (2013.01); *A61K 31/4196* (2013.01); *A61K 47/10* (2013.01); *A61K 47/12* (2013.01); *A61K 47/24* (2013.01); *A61K 47/34* (2013.01); *A61Q 7/00* (2013.01); *A61Q 19/00* (2013.01); *A61Q 19/08* (2013.01)

(58) Field of Classification Search
CPC ...... A61K 9/0014; A61K 9/107; A61K 47/10; A61K 47/12; A61K 47/34; A61K 47/24
See application file for complete search history.

(56) References Cited

FOREIGN PATENT DOCUMENTS

| | | | |
|---|---|---|---|
| WO | WO-2011/070318 | 6/2011 | |
| WO | WO-2011070318 A2 * | 6/2011 | ........... A61K 9/0014 |
| WO | WO-2013/142472 A2 | 9/2013 | |

OTHER PUBLICATIONS

Sene et al. (Product Information—Technical paper, Dow Corning Corporation, USA, No. 52-1034-01, 2002, pp. 1-12) (Year: 2002).*
Dow Corning 9040 (Product Information, Sep. 26, 2014) (Year: 2014).*
Dow Corning EL-7040 (Product Information, Nov. 5, 2013) (Year: 2013).*
Soltanpour et al. (J Solution Chem (2011) 40:2032-2045). (Year: 2011).*
Anonymous: "Product Information: Dow Corning EL-7040 Hydro Elastomer Blend", Nov. 5, 2013, retrieved from the Internet: http://www.dowcorning.co.jp/DataFiles/090276fe8019078a.pdf.
Carroll, C.L., et al., "Adherence to topical therapy decreases during the course of an 8-week psoriasis clinic trial: commonly used methods of measuring adherence to topical therapy overestimate actual use." Journal of the American Academy of Dermatology 51, 212-216 (2004).
Cohen, et al., "Nonattendance in a dermatology clinic—a large sample analysis." Journal of the European Academy of Dermatology and Venereology: JEADV 22, 1178-1183 (2008).
Davis, S.A., et al., "Using Hawthorne effects to improve adherence in clinical practice: lessons from clinical trials." JAMA dermatology 149, 490-491 (2013).
Devaux, S., et al., "Adherence to topical treatment in psoriasis: a systematic literature review." Journal of the European Academy of Dermatology and Venereology: JEADV 26 Suppl 3, 61-67 (2012).
Dow Corning et al., "Product Information Personal Care 9040 Silicone Elastomer Blend," Sep. 26, 2014, retrieved from the Internet: URL:http://www.dowcorning.com/DataFiles/090276fe801bf9c7.pdf.
Feldman, S.R., et al., "Topical clobetasol propionate in the treatment of psoriasis: a review of newer formulations." American journal of clinical dermatology 10, 397-406 (2009).
International Search Report and Written Opinion issued on PCT/GB2016/050545, dated May 31, 2016.
Krejci-Manwaring, J., et al., "Adherence with topical treatment is poor compared with adherence with oral agents: implication for effective clinical use of topical agents." Journal of the American Academy of Dermatology 54, S235-236 (2006).
Krejci-Manwaring, J., et al., "Stealth monitoring of adherence to topical medication: adherence ins very poor in children with atopic dermatitis." Journal of the American Academy of Dermatology 56, 211-216 (2007).

(Continued)

Primary Examiner — Theodore R. West
(74) Attorney, Agent, or Firm — Foley & Lardner LLP

(57) ABSTRACT

A formulation for topical dermatological delivery of a medicinal or cosmeceutical or cosmetic active including a functional co-enhancer delivery system. The delivery system generally comprises a water-miscible solvent and $C_{12}$ or $C_{14}$ fatty acids or $C_{14}$ alcohol in combination with a hydrocarbyl methyl siloxane emollient.

29 Claims, 11 Drawing Sheets

(56) References Cited

OTHER PUBLICATIONS

Lehman, P.A., et al., "Assessing topical bioavailability and bioequivalence: a comparison of the in vitro permeation test and the vasoconstrictor assay." Pharmaceutical research 31, 3529-3537 (2014).
Newton et al.,j "Silicone Technology Offers Novel Methods for Delivering Active Ingredients," SOFW—Journal Seifen, vol. 130, No. 5, May 25, 2004.
Sabaté E., "Adherence to Long-Term Therapies: Evidence for Action." (2003).
Sene C et al., "Silicones as Excipients for Topical Pharmaceutical Applications—The Silky Touch Product Family from Dow Corning," Product Information Technical Paper, Dow Corning Corporation, USA, No. 52-1034-01, 2002, pp. 1-12.
Storm, A., et al, "One in 3 prescriptions are never redeemed: primary nonadherence in an outpatient clinic." Journal of the American Academy of Dermatology 59, 27-33 (2008).
Tan, X., et al., "Topical drug delivery systems in dermatology: a review of patient adherence issues." Expert opinion on drug delivery 9, 1263-1271 (2012).
Warino, L., et al., "Clobetasol propionate for psoriasis: are ointments really more potent?" Journal of drugs in dermatology: JDD 5, 527-532 (2006).
Zschocke, I., et al., "Non-adherence and measures to improve adherence in the topical treatment of psoriasis." Journal of the European Academy of Dermatology and Venereology: JEADV 28 Suppl 2, 4-9 (2014).

\* cited by examiner

FIG. 11

Table 1 Formulations: Examples with PG:G 80:20 and Myristyl alcohol (MAlc, C14 alcohol).

| Material | % w/w Formulation #1 | % w/w Formulation #2 | % w/w Formulation #3 | % w/w Formulation #4 | % w/w Formulation #5 | % w/w Formulation #6 | % w/w Formulation #7 | % w/w Formulation #8 | % w/w Formulation #9 | % w/w Formulation #10 |
|---|---|---|---|---|---|---|---|---|---|---|
| Active agent (@0.05%) | 0.00 | 0.00 | 0.00 | 0.00 | 0.00 | 0.00 | 0.00 | 0.00 | 0.00 | 0.00 |
| Propylene glycol (PG) | 23.16 | 23.16 | 25.00 | 30.00 | 35.00 | 40.00 | 25.00 | 25.00 | 25.00 | 25.00 |
| Glycerol (G) | 5.79 | 5.79 | 6.25 | 7.50 | 8.75 | 10.00 | 6.25 | 6.25 | 6.25 | 6.25 |
| Myristyl alcohol (1) | - | 0.60 | 0.60 | 0.60 | 0.60 | 0.60 | 0.60 | 0.60 | 0.60 | 0.60 |
| ST Elastomer | 25.00 | 25.00 | 25.00 | 25.00 | 25.00 | 15.00 | 25.00 | 25.00 | 25.00 | 25.00 |
| STE polymer 12.50% | (3.125) | (3.125) | (3.125) | (3.125) | (3.125) | 1.875 | (3.125) | (3.125) | (3.125) | (3.125) |
| STE solvent S-NF 87.50% | (21.875) | 21.875 | (21.875) | (21.875) | (21.875) | 13.125 | (21.875) | (21.875) | (21.875) | (21.875) |
| EL-7040 | 25.00 | 25.00 | 22.7 | 16.45 | 10.20 | 13.95 | 18.7 | 18.7 | 21.7 | 20.7 |
| EL-7040 polymer 18.5% | (4.625) | (4.625) | (4.1995) | (3.04325) | (1.887) | 2.58075 | (4.1995) | (4.1995) | (4.0145) | (3.8295) |
| EL-7040 CM 81.5% | (20.375) | (20.375) | (18.5005) | (13.40675) | (8.313) | 11.36925 | (18.5005) | (18.5005) | (17.6855) | (16.8705) |
| Myristyl alcohol (2) | 0.40 | 0.40 | 0.40 | 0.40 | 0.40 | 0.40 | 0.40 | 0.40 | 0.40 | 0.40 |
| DC 0.65 | 20.00 | 20.00 | 20.00 | 20.00 | 20.00 | 20.00 | 20.00 | 20.00 | 20.00 | 20.00 |
| DC 20 (DC Q7-9120) | - | - | - | - | - | - | - | - | - | 2.00 |
| DC 100 (DC Q7-9120) | - | - | - | - | - | - | 4.00 | - | 1.00 | - |
| DC 350 (DC Q7-9120) | - | - | - | - | - | - | - | 4.00 | - | - |
| Total | 98.95 | 99.95 | 99.95 | 99.95 | 99.95 | 99.95 | 99.95 | 99.95 | 99.95 | 99.95 |
| Comment | -De enhancer | +MAlc De enhancer | +MAlc De enhancer ↑ PG:G 80:20 | +MAlc De enhancer ↑↑ PG:G 80:20 | +MAlc De enhancer ↑↑↑ PG:G 80:20 | +MAlc De enhancer ↑↑↑↑ PG:G 80:20 | #3 + DC100 4% | #3 + DC350 4% | #3 + DC100 1% | #3 + DC20 2% |
| Lab code / details | #1 10/11/14 pump | #1 11/11/14 pump | #1 12/11/14 pump | #2 12/11/14 pump | #3 12/11/14 jar | #4 12/11/14 jar | #5 12/11/14 jar | #6 12/11/14 jar | #1 13/11/14 pump | #1 15/11/14 jar |

FIG. 12
Table 2 Formulations: Examples with PG:G 80:20 and Myristyl alcohol (MAlc, C14 alcohol), Myristic acid (MA, C14 acid) and Lauric acid (LA, C12 acid).

| Material | % w/w Formulation #3 (control) | % w/w Formulation #11 | % w/w Formulation #12 | % w/w Formulation #13 |
|---|---|---|---|---|
| Active Agent (@0.05%) | 0.00 | 0.00 | 0.00 | 0.00 |
| Propylene glycol (PG) | 25.00 | 25.00 | 25.00 | 25.00 |
| Glycerol (G) | 6.25 | 6.25 | 6.25 | 6.25 |
| Myristyl alcohol, MAlc (1) | 0.60 | - | 0.60 | - |
| Myristic acid, MA (1) | - | 0.31 | 0.31 | - |
| Lauric acid, LA (1) | - | - | - | 1.635 |
| ST Elastomer | 25.00 | 25.00 | 25.00 | 25.00 |
| STE polymer 12.50% | (3.125) | (3.125) | (3.125) | (3.125) |
| STE solvent 5-NF 87.50% | (21.875) | (21.875) | (21.875) | (21.875) |
| EL-7040 | 22.7 | 23.21 | 22.21 | 21.34 |
| EL-7040 polymer 18.5% | (4.1995) | (4.29385) | (4.10885) | (3.9479) |
| EL-7040 CM 81.5% | (18.5005) | (18.91615) | (18.10115) | (17.3921) |
| Myristyl alcohol, MAlc (2) | 0.40 | - | 0.40 | - |
| Myristic acid, MA(2) | - | 0.18 | 0.18 | - |
| Lauric acid LA (2) | - | - | - | 0.725 |
| DC 0.65 | 20.00 | 20.00 | 20.00 | 20.00 |
| Total | 99.95 | 99.95 | 99.95 | 99.95 |
| Comment | MAlc Dc enhancer ↑ PG:G 80:20 (from Table #1) | MA Dc enhancer ↑ PG:G 80:20 | +MAlc +MA Dc enhancers ↑ PG:G 80:20 | +LA Dc enhancer ↑ PG:G 80:20 |
| Lab code /details | #1 12/11/14 pump | #2 15/11/14 jar | #3 15/11/14 jar | #4 15/11/14 jar |

FIG. 13
Table 3 Active formulations: Examples with PG:G 80:20 and Myristyl alcohol (MAlc, C14 alcohol).

| Material | % w/w Formulation #3 | % w/w Formulation #14 | % w/w Formulation #15 | % w/w Formulation #16 | % w/w Formulation #16.a |
|---|---|---|---|---|---|
| Fluticasone propionate | 0.00 | 0.005 (FP) | - | - | - |
| Mometasone furoate | 0.00 | - | 0.010 (MF) | - | - |
| Betamethasone propionate | 0.00 | - | - | - | 0.05 |
| Retinoic acid | 0.00 | - | - | 0.005 (ATRA) | - |
| Propylene glycol (PG) | 25.00 | 25.00 | 25.00 | 25.00 | 25.00 |
| Glycerol (G) | 6.25 | 6.295 | 6.295 | 6.295 | 6.25 |
| Myristyl alcohol (1) | 0.60 | 0.60 | 0.60 | 0.60 | 0.90 |
| ST Elastomer | 25.00 | 25.00 | 25.00 | 25.00 | 23.75 |
| STE polymer 12.50% | (3.125) | (3.125) | (3.125) | (3.125) | |
| STE solvent 5-NF 87.50% | (21.875) | (21.875) | (21.875) | (21.875) | |
| EL-7040 | 22.7 | 22.7 | 22.7 | 22.45 | 23.45 |
| EL-7040 polymer 18.5% | (4.1995) | (4.1995) | (4.1995) | (4.15325) | |
| EL-7040 CM 81.5% | (18.5005) | (18.5005) | (18.5005) | (18.29675) | |
| Myristyl alcohol (2) | 0.40 | 0.40 | 0.40 | 0.40 | 0.60 |
| DC 0.65 | 20.00 | 20.00 | 20.00 | 20.0 | 20.0 |
| BHT | - | - | - | 0.25 | - |
| Total | 99.95 | 100.00 | 100.00 | 100.00 | 100.00 |
| Comment | +MAlc De enhancer ↑ PG:G 80:20 (from Table #1) | +MAlc De enhancer ↑ PG:G 80:20 Fluticasone propionate | +MAlc De enhancer ↑ PG:G 80:20 Mometasone furoate | +MAlc De enhancer ↑ PG:G 80:20 Retinoic acid | +MAlc De enhancer ↑ PG:G 80:20 Betamethasone diprop. |
| Lab code / details | #1 12/11/14 pump | #5 15/11/14 pump | #6 15/11/14 pump | #1 03/12/14 pump | #1 16/07/15 pump |

FIG. 14

Table 4: Formulations: Examples using propylene glycol, pentylene glycol, hexylene glycol and Transcutol as PC enhancer.

| Material | Formulation #17 | Formulation #17a | Formulation #18 | Formulation #19 | Formulation #20 |
|---|---|---|---|---|---|
| Active Agent (@0.05/50) | 0.00 | 0.00 | 0.00 | 0.00 | 0.00 |
| Propylene glycol | 12.50 | 15.625 | - | - | - |
| Pentylene glycol | - | - | 12.50 | - | - |
| Hexylene glycol | - | - | - | 12.50 | - |
| Transcutol P | - | - | - | - | 12.50 |
| Glycerol | 3.125 | - | 3.125 | 3.125 | 3.125 |
| Myristyl alcohol (1+2) | 0.75 | 0.75 | 0.75 | 0.75 | 0.75 |
| EL-7040 | 14.00 | 14.00 | 14.00 | 14.00 | 14.00 |
| ST Elastomer 0.65 | 9.00 | 9.00 | 9.00 | 9.00 | 9.00 |
|  | 10.575 | 10.575 | 10.575 | 10.575 | 10.575 |
| total | 49.95 | 49.95 | 49.95 | 49.95 | 49.95 |
| Comments | Appearance as standard | Appearance as standard | Appearance as standard | Thinner than standard | Thinner than standard |
| Lab code / details | #1 14/02/15 pump pack | #2 14/02/15 pump pack | #3 14/02/15 pump pack | #4 14/02/15 pump pack | #4514/02/15 pump pack |

FIG. 15
Table 5: Formulations: Examples using dimethicone ST elastomer and dimethicone macromer emulsifier blends

| Material | Formulation #21 | Formulation # 22 | Formulation #23 | Formulation #24 | Formulation #25 | Formulation #26 |
|---|---|---|---|---|---|---|
| Active Agent (@0.10/50g) | 0.00 | 0.00 | 0.00 | 0.00 | 0.00 | 0.00 |
| Propylene glycol | 12.50 | 12.50 | 12.50 | 12.50 | 12.50 | 12.50 |
| Glycerol | 3.125 | 3.125 | 3.125 | 3.125 | 3.125 | 3.125 |
| NaCl | - | 0.50 | 0.50 | 0.50 | 0.50 | - |
| Myristyl alcohol (1+2) | 0.50 | 0.50 | 0.50 | 0.50 | 0.50 | 0.50 |
| ST Elastomer | 12.00 | 12.00 | 12.00 | 12.00 | 12.00 | 12.00 |
| EL-7040 | 12.00 | 12.00 | 12.00 | - | - | 11.00 |
| DC 5225C (Cyclopentasiloxane, PEG/PPG-18/18 dimethicone) | - | - | 5.00 | - | - | - |
| TI-6021 (PEG-10 dimethicone) | - | - | - | 2.00 | - | - |
| DC 9011 (PEG-12 dimethicone crosspolymer, cyclopentasiloxane) | - | - | - | - | 12.00 | - |
| PCA dimethicone | - | - | - | - | - | 1.00 |
| Caprylyl methicone | - | - | - | 10.00 | - | - |
| 5-NF | - | - | - | 9.375 | - | - |
| 0.65 | 9.775 | 9.275 | 4.275 | - | 9.275 | 9.775 |
| total | 49.90 | 49.90 | 49.90 | 50.00 | 49.90 | 49.90 |
| Comments | #1 29/08/15 pump pack | #2 29/08/15 pump pack | #3 29/08/15 pump pack | #1 05/09/15 pump pack | #4 05/09/15 pump pack | #1 28/02/16 |
| Lab code / details | Control #3 18/07/15 | +NaCl control good aesthetic | + PEG/PPG-18/18 dimethicone | + PEG-10 dimethicone | + PEG-12 dimethicone crosspolymer | +PCA dimethicone |

FIG. 16
Table 6: Formulations: Examples using water and ethanol as highly volatile solvents.

| Material | Formulation #1 | Formulation #2 | Formulations #3 | Formulations #4 | Formulations #5 | Formulations #6 |
|---|---|---|---|---|---|---|
| Active Agent | 0.05 (Candidate active) | 0.05 (Candidate active) | 0.05 (Candidate active) | 2.00 (Lactobionic acid) | 1.00 (Salicylic acid) | 0.00 |
| Propylene glycol | 12.5 | 12.5 | 12.5 | 12.50 | 7.50 | 12.50 |
| Glycerol | 3.125 | 1.39 | 0 | 3.15 | 6.00 | 3.15 |
| Water | 5 | 5 | 5 | 10.00 | 6.25 | 5.00 |
| Ethanol | 7.5 | 7.5 | 7.5 | - | 5.00 | 5.00 |
| Myristyl alcohol (1+2) | 0.75 | 0.75 | 0.75 | 0.75 | 0.75 | 0.75 |
| ST Elastomer | 7.075 | 8.81 | 10.2 | 12.50 | 12.50 | 12.50 |
| EL-7040 | 14 | 14 | 14 | 11.0 | 11.00 | 11.00 |
| Carbopol Ultrez-10 | - | - | - | - | - | 0.20 |
| 18% KOH | - | - | - | - | - | 0.10 |
| Total | 50 | 50 | 50 | 51.90 | 50.00 | 50.20 |
| Comments | PG:G 80:20, excellent aesthetic | PG:G 90:10, excellent aesthetic | PG:G 100:0, excellent aesthetic | PG:G 80:20, good aesthetic | PG:G 55:45, good aesthetic | PG:G 80:20, excellent aesthetic |
| Lab code/details | #1 13/02/15 Pump pack | #2 13/02/15 Pump pack | #3 13/02/15 Pump pack | #1 03/04/15 Pump pack | #1 02/04/15 Pump pack | #1 19/02/15 Pump pack |

TOPICAL FORMULATION

CROSS REFERENCE TO RELATED APPLICATIONS

This application is the U.S. national phase application under 35 U.S.C. § 371 of International Application No. PCT/GB2016/050545, filed Mar. 3, 2016, which claims priority to GB Application 1503590.0, filed Mar. 3, 2015, the contents of which are incorporated herein by reference in their entireties.

The present invention relates to topical formulations comprising a pharmaceutical, cosmeceutical or cosmetic active which have good absorption into the skin and underlying tissue, thus which cross the stratum corneum effectively, allowing efficient and predictable delivery of the active to a patient. The formulations of the present invention generally comprise one or more diol partition coefficient (PC) enhancers, at least two dimethicone macromers, one or more diffusion coefficient (DC) enhancers selected from the group consisting of $C_{12}$-$C_{14}$ acid and $C_{14}$ alcohol and an emollient siloxane. The invention also relates to a method of treatment and a process for preparing such formulations.

The topical formulations of the present invention have surprisingly good skin-feel, promoting patient adherence to methods of medical or cosmetic treatment, and thus improving the associated therapeutic outcome. Especially in anhydrous formulation variants, the chemical stability of sensitive agents is substantially increased.

BACKGROUND TO THE INVENTION

Unmet Patient and Consumer Needs

In its 2003 report on medication adherence[1], the World Health Organization (WHO) asserts that "increasing the effectiveness of adherence interventions may have a far greater impact on the health of the population than any improvement in specific medical treatments." In this report, WHO were mainly concerned with major systemic diseases and subsequent, mainly oral, therapies. Several factors related to therapy were found to be associated with poor adherence, these include: slow onset or intensity of benefit, actual or perceived unwanted effects and treatment regimens inconsistent with lifestyle. Since this 2003 WHO Report, several studies have investigated the incidence of poor adherence and its causes for topical dermatological medicines.

Topical application of medicines to the skin to treat conditions and diseases of the skin and the underlying tissues is an intuitive therapeutic concept; it makes sense. Topical products are widely and enthusiastically used by consumers as evidenced by the $110 billion 2014 worldwide annual sale of skin care products in the cosmetic beauty market. Yet, adherence to recommended or prescribed topical dermatological medicinal products is disappointingly low. For example, Cohen et al.[2] (2008) reported that 26% of over 7,000 dermatology clinic outpatients did not show up for their first appointment. Storm et al.[3] (2008) found that one-in-three dermatological outpatient clinic prescriptions were not picked up by patients. In an 8-week monitored clinical trial (Carroll et al., 2004), patient self-reported logs record 80-90% adherence to the recommended dose regimen, whereas electronic stealth monitoring in pack, showed actual adherence to be at around 40%.[4] Also, in such clinical trials or outpatient-monitored treatments, the Hawthorn effect (Davis and Feldman, 2013; Krejci-Manwaring et al.)[5,6], the change in behaviour of patients when they are monitored more closely, will work to improve adherence. Feldman and Yentzer[7] (2009) believe that adherence to treatment is an important determinant of success, especially in actual clinical use as opposed to the well-controlled environment of clinical trials Adherence to general-practitioner-prescribed topical dermatologicals is not yet reported, yet the concern is that this will be around 20% or lower.

Poor adherence does not seem to be a problem peculiar to dermatology patients. Krejci-Manwaring[8] (2006) reported that electronically monitored adherence of dermatology patients to an oral medication, was up to 80% after three weeks treatment, compared to 20% for a topical medication.

Research into the reasons for these low rates of adherence identifies, much as the WHO Report, that slow and poor response to treatment, incidence of or fear of incidence of local and systemic drug adverse effects (especially the phobia of topical corticosteroids), treatment regimens inconsistent with lifestyle and, specific to topical products, the poor aesthetics and experience in use of topical dermatological products, are main causal factors (Zschocke et al. 2014, Tan et al. 2012, Devaux et al. 2012)[9-11].

It might be expected that efficacy and safety issues would be the main drivers of topical dermatological non-adherence, but this does not appear to be the case. Recent clinical reviews (Warino and Feldman et al. 2006[12]; Feldman and Yentzer 2009[7]) conclude that efficacy rates in psoriasis for emollient-type formulations of clobetasol propionate are equivalent to those obtained with the more potent clobetasol propionate ointment formulation (Temovate) owing to the much improved aesthetics of the emollient-type formulations.

Passive Topical Drug Delivery Technology: Principles and Limitations

Ointment, gel, cream and emollient cream Temovate formulations of clobetasol propionate all contain 0.05% w/w of the active. Lehman and Franz[13] measured the in-vitro flux of clobetasol propionate across human skin from 0.05% Temovate ointment, gel, cream and emollient cream products. Peak fluxes across the skin were 70, 25, 25 and 5 $ng/cm^2/hour$, respectively, consistent with the ointment being widely regarded as the most potent formulation. The emollient in Temovate emollient cream is isopropyl myristate, which is an excellent solvent for corticosteroids. The much lower skin flux measured from the emollient cream is due to solubilisation of the active by isopropyl myristate such that it is held within the applied film on the skin and skin penetration is greatly reduced. A fundamental principle of passive topical delivery is that the thermodynamic activity of the active, otherwise expressed as its degree of saturation in the vehicle, should be high to maximise skin penetration. Thus, a limitation of current technologies is their inability to incorporate emollients and yet maintain a high degree of saturation of the active and thus optimized skin penetration.

More recent passive delivery coenhancer technologies, addressing all of the principles embodied in Fick's first law of diffusion represent the current the state-of-the art as they provide:

the active at or near saturation
inclusion of a partition coefficient enhancer
inclusion of a diffusion coefficient enhancer, also at or near saturation U.S. Pat. No. 8,541,470 describes such a coenhancer composition for topical application of an NSAID, which comprises a solution or suspension of the NSAID in a carrier system comprising a polyhydric alcohol, a glycol ether and an ester of a higher fatty acid, the carrier system being present as a single phase at ambient temperatures. The NSAID may be diclofenac as diclofenac acid. The polyhydric alcohol may be a glycol such as isopropylene glycol and the glycol ether may be a diethylene glycol ether such as diethylene glycol monoethyl ether. The higher fatty acid is generally isopropyl myristate.

The formulation described in U.S. Pat. No. 8,541,470 is designed around a nonvolatile single-phase residual phase comprising the active and functional partition coefficient, (for example, propylene glycol) and diffusion coefficient (for example, isopropyl myristate) coenhancer excipients together with a cosolvent (diethylene glycol monoethyl ether). Skin penetration of the active is primarily dependent upon:

- the dose of the partition coefficient enhancer
- the degree of saturation of the active in the nonvolatile single phase residual phase
- the degree of saturation of the diffusion coefficient enhancer in the nonvolatile single phase residual phase.

To complete such coenhancer-type formulations, highly volatile solvents and a gelation polymer may be added to the nonvolatile residual phase to ensure appropriate macro-viscosity and ease of application in use. On application to the skin, evaporation of the highly volatile solvents quickly reforms the essential physicochemistry of the nonvolatile single-phase residual phase.

Although it was well known to consider the degree of saturation of the active, U.S. Pat. No. 8,541,470 describes the importance of the degree of saturation of the diffusion coefficient enhancer, generally isopropyl myristate, in the nonvolatile residual phase. FIG. 1 of U.S. Pat. No. 8,541,470 is a ternary phase diagram which describes those compositions of the nonvolatile single-phase residual phase in which the diffusion coefficient enhancer is at saturation. If the degree of saturation of the diffusion coefficient enhancer is low, a significant reduction in skin penetration of the active is observed.

Despite their drug delivery benefits, coenhancer formulations such as those described in U.S. Pat. No. 8,541,470 are associated with poor rub-in and skin feel, being associated with tackyness and skin drying.

In the previous section it was shown that poor aesthetics and experience in use of topical dermatological products were main causal factors in poor adherence. Coenhancer systems formulated as emollient creams would address several of the factors driving poor adherence. However, addition of the surfactant and emollient oil phase of a cream tends to affect the performance of an included coenhancer system, leading to poor penetration of the active through the skin barrier, and thus poor delivery of the active compound to the target site.

Without being bound by theory, we hypothesise that this is because the surfactant and emollient oil phase of the cream have detrimental effects of on the performance of the coenhancer system. Particularly, emollient oil phase components comprising hydrocarbon structural elements might be expected to solubilise diffusion coefficient-enhancing excipients, such as those comprising alcohols, acids or esters derivatives of $C_8$-$C_{22}$ hydrocarbons. Ideally, the diffusion coefficient enhancer should be at or near saturated solubility in the nonvolatile residual phase of the formulation. Emollient excipients that lead to an increase in the solubility of the diffusion coefficient enhancer in the residual nonvolatile emollient oil phase of the vehicle, such that the diffusion coefficient enhancer becomes grossly subsaturated, might be expected to adversely affect the partitioning of the diffusion coefficient enhancer into the stratum corneum barrier and to reduce skin penetration of an incorporated active by 5-10 fold.

Thus, a limitation of current coenhancer technologies is their inability to incorporate emollients and yet maintain degree of saturation of the diffusion coefficient enhancer and thus optimized skin penetration.

The present invention seeks to provide topical formulations with outstanding rub in and skin feel and with enhanced skin penetration allowing efficient and predictable delivery of the active compound to the target site of delivery, thus to increase patient and consumer adherence,

STATEMENT OF INVENTION

A first aspect of the invention provides a formulation for topical application comprising:

- an active compound,
- a partition coefficient enhancer (PC enhancer), generally in the form of a primary or secondary alcohol, typically a diol compound;
- a diffusion coefficient enhancer (DC enhancer) selected from the group consisting of a $C_{12}$ to $C_{14}$ straight chain fatty acid and a $C_{14}$ straight chain primary alcohol;
- a first dimethicone macromer mixture including a dimethicone macromer and a hydrocarbyl methyl siloxane emollient selected from the group consisting of an alkyl methyl siloxane, an aryl methyl siloxane and an alkyl aryl methyl siloxane; and
- a second dimethicone macromer mixture including a methyl siloxane compound and a cross-linked dimethicone macromer.

Because both typical actives and the selected DC enhancers have appropriate solubility in the hydrocarbyl methyl siloxane emollient the formulation of the present invention allows efficient delivery of the active through the stratum corneum and to the underlying tissue. This efficient delivery allows that a reduced amount of the active compound in the formulation of the present invention is needed to achieve a therapeutic or cosmetic effect. There is thus a reduced risk of adverse reaction to the active compound. Less active compound is required to achieve a therapeutic effect compared to known formulations, resulting in reduced waste, and reduced associated cost.

Surprisingly the incorporation of two dimethicone macromers increases the physical stability of the resultant formulation. Without being bound by theory, the inventor believes this may be due to increased viscosity of the film at the interface of the dispersed and continuous phases.

The formulation of the present invention has a very good associated skin feel. In particular, the formulation of the present invention has good spreadability and slip on the skin and skin to which the formulation has been applied is associated with increased smoothness and softness. Accordingly, patient adherence to a method of treatment involving application of the formulation is increased resulting in a better medical outcome.

According to a further aspect of the present invention there is provided a cosmetic composition comprising any of the formulations described herein and one or more pharmaceutically acceptable carriers or excipients.

According to a further aspect of the present invention there is provided a cosmeceutical composition comprising any of the formulations described herein and one or more pharmaceutically acceptable carriers or excipients.

According to a further aspect of the present invention there is provided a pharmaceutical composition comprising any of the formulations described herein and one or more pharmaceutically acceptable carriers or excipients.

There is also provided any of the formulations or compositions as disclosed herein for use in therapy.

According to a further aspect of the present invention there is provided a method of preventing, reducing the likelihood of, alleviating or treating a medical condition in the human or animal body comprising the topical administration in a therapeutically effective amount of any of the formulations described herein.

According to a further aspect of the present invention, there is provided any of the formulations as described herein for use in the prevention, alleviation or treatment of a medical condition of the human or animal body.

The medical condition may be selected from the group consisting of conditions associated with or caused by one or more of pain and/or inflammation, pruritus, acne, eczema, psoriasis, rosacea, nappy rash, dry skin, microbial conditions including fungal and/or bacterial conditions such as skin infections including yeast infections and dermatophyte infections, dry or ageing skin, sun spots and alopecia. The medical condition is generally treated by topical application.

According to a further aspect of the present invention, there is provided a method of forming the composition as described herein. The components of the formulation are mixed together to homogeneity. Generally the active compound is added in the form of a solution. Typically the DC enhancer is added in the form of a solution.

According to a further aspect of the present invention, there is provided a kit of parts for use in the prevention, alleviation or treatment of a medical condition of the human or animal body, said kit of parts including any of the formulations described herein and an applicator device such as a syringe, spatula, or spray device. The kit of parts generally includes instructions for use.

The composition is generally applied to the biological membrane, in particular the skin of the human or animal body, including the mucous membranes of the human or animal body.

Definitions

Ambient temperature denotes the range 20 to 26° C., with an average temperature of 23 to 25° C., generally around 23° C.

The term "good skin feel" is used to relate to a formulation which is generally easily absorbed into the skin to leave the skin feeling smoother and/or softer than prior to application of the formulation. A formulation associated with good skin feel would typically leave the skin non-greasy and silky.

By an "effective" amount or "therapeutically effective amount" is meant an amount of one or more active substances which, within the scope of sound medical judgment, is sufficient to provide a desired effect without excessive toxicity, irritation, allergic response, or other problem or complication, commensurate with a reasonable benefit/risk ratio.

All numerical values provided incorporate 0% by weight less than and 10% by weight more than the numerical value provided.

A partition coefficient is the ratio of amounts of a substance in a mixture of two immiscible phases at equilibrium. The partition coefficient may be calculated according to the expression below:

$$K_{partition}=[X_{(phase\ 1)}]/[X_{(phase\ 2)}]$$

Where K is the partition coefficient, X is the substance, $X_{(phase\ 1)}$ is the amount of substance in the first phase and $X_{(phase\ 2)}$ is the amount of substance in the second phase.

As used herein, a partition coefficient (PC) enhancer increases the partition coefficient of an active compound between the non-volatile residual phase of the formulation and the stratum corneum barrier layer of the skin, thus enhancing the penetration of the active compound to the target site in or below the skin.

As used herein, a diffusion coefficient (DC) enhancer increases the diffusion coefficient of an active compound within the stratum corneum barrier layer of the skin, thus enhancing the penetration of the active compound to the target site in or below the skin.

The partition coefficient (PC) enhancer and diffusion coefficient (DC) enhancer affect penetration of the active compound to the target site in or below the skin as defined by Fick's First Law of Diffusion $$F=Cv*PC*DC/h$$

where F is the flux, the mass of agent penetrating the stratum corneum per unit time per unit area, Cv is the concentration of active in solution in the non-volatile residual phase, PC refers to the partition coefficient enhancer effect, DC refers to the diffusion coefficient enhancer effect and h is the thickness of the stratum corneum barrier.

Preferably, the modified form of Fick's First Law of Diffusion is used in formulation design:

$$F=\sim DS_v*\text{sat sol }SC*DC/h$$

where F is the flux, the mass of agent penetrating the stratum corneum per unit time per unit area, $DS_v$ is the degree of saturation of the active in solution in the non-volatile residual phase, sat sol SC is the saturated solubility of the active in the stratum corneum (as affected by the partition coefficient enhancer), DC refers to the diffusion coefficient enhancer effect and h is the thickness of the stratum corneum barrier.

For the purpose of the current invention; by the term highly volatile are described liquids such as Dow Corning® Q7-9180 Silicone Fluid (0.65 cSt, hexamethyldisiloxane and 1.0 cSt, octamethyltrisiloxane), ethanol, isopropyl alcohol and water which have half-lives of evaporation at skin temperature of under 5 minutes, by the term volatile are described liquids such as cyclopentacyloxane (D5) which have half-lives of evaporation at skin temperature of approximately 1 hour and by the term nonvolatile are described liquids such as caprylyl methicone and polydimethylsiloxanes (Dow Corning Q7-9120 silicone fluids) which have half-lives of evaporation at skin temperature of approximately 24 hours or greater. Formulations of the current invention are intended for application once or twice a day.

The term "non-volatile residual phase" describes the composition of the formulation remaining after evaporation of volatile solvents such as Dow Corning® Q7-9180 Silicone Fluid (0.65 cSt and 1.0 cSt), ethanol, isopropyl alcohol and water and thus generally comprises the active agent, PC enhancer, DC enhancer and medium and high molecular weight materials. As used herein, the nominally volatile silicones ST cyclomethicone 5-NF and alkyl methyl siloxanes such as caprylyl methicone are considered non-volatile in the context of the time frame of topical application and absorption.

The term "carbinol" is used to refer to a hydroxyl functional group attached to a carbon atom. The carbon atom may be attached to a carbon atom (in particular a carbon atom forming part of a hydrocarbon group), a non-carbon atom including Si, N and O.

The term "small alkyl group" refers to an alkyl group having a carbon backbone of 1 to 6 carbon atoms, typically 1 to 4 carbon atoms.

Formulation

A first aspect of the invention provides a formulation for topical application comprising:
an active compound,
a partition coefficient enhancer (PC enhancer), having a structure of the general formula: $C_nH_{2n+2}O_2$ where n represents an integer from 3 to 6 inclusive,
a diffusion coefficient enhancer (DC enhancer) selected from the group consisting of a $C_{12}$ to $C_{14}$ straight chain fatty acid and a $C_{14}$ straight chain primary alcohol,
a first dimethicone macromer mixture including a dimethicone macromer and a hydrocarbyl methyl siloxane emollient selected from the group consisting of an alkyl methyl siloxane, an aryl methyl siloxane and an alkyl aryl methyl siloxane, and
a second dimethicone macromer mixture including a methyl siloxane compound and a cross-linked dimethicone macromer.

Generally the formulation is a water-in-silicone or polyol-in-silicone mixture, in particular a polyol-in-silicone emulsion.

According to one embodiment, the present invention provides a formulation suitable for the topical application of the active compound, the formulation comprising the active compound in a carrier, wherein the carrier comprises a partition coefficient enhancer comprising a secondary or primary alcohol group, a diffusion coefficient enhancer selected from the group consisting of a $C_{12}$ to $C_{14}$ fatty acid and a $C_{14}$ alcohol, a first dimethicone macromer mixture and a second cross-linked dimethicone macromer mixture.

Generally the formulation comprises a solution, suspension or dispersion of the active compound in the carrier. Preferably the active is in solution.

The formulation of the present invention achieves and improves efficacy of active delivery, promoting adherence. In particular, the formulation of the present invention provides enhanced skin penetration compared to known formulations, allowing a high therapeutic free active compound concentration at the target site to be achieved and sustained. Generally the free active compound concentration at the target site is significantly above the EC50 (half maximal effective concentration). The efficacy of the delivery of the active compound to the target site is maximised, producing an efficacious, robust treatment regime. Severe conditions may thus be treated or a more robust clinical response may be achieved in the general patient population.

The extent of absorption of the majority of dermatological actives is in the range 1-5% of the dose applied on normal skin. At permeable skin sites the dose absorbed increases markedly and is associated with local and systemic adverse effects. The formulation of the present invention provides controlled dosing of the active compound, reducing the potential of adverse effects, this also promotes adherence. As the delivery of the active compound to the target site is optimized through the use of the formulation of the present invention, the dose of active compound contained in the formulation may be reduced, typically to 5-10% of current doses. This reduces the risk and fear of adverse effects, maximizing adherence to the method of medical treatment, and reduces the waste and associated cost of excessive dosing in less efficacious drug delivery systems. Histori-cally, this has been seen as an economic issue of wastage, to which might now be added the environmental issue of pollution caused by washing off and release into the environment of the excess drug. Primarily, this is a major therapeutic issue.

The formulation of the present invention is sufficiently efficacious to allow reduced dosing, reducing the necessity of applying known formulations 2 to 6 times per day to 1 to 3 times per day, generally once daily. Single daily treatments or intermittent treatment regimens are universally appreciated by patients and consumers, and are supported in science by drug depot formation within the stratum corneum. The formulation of the present invention allows the possibility of such dosage regimes whilst retaining the efficacy of the treatment and this promotes adherence.

It has consistently been found that users prefer creams to gel and ointment formulations.

Emollients are the main functional aesthetic components within creams usually requiring surfactant and wax co-excipients for effective dispersion. Emollients bring cosmetic attributes of spreadability, slip and smoothness, which drive adherence. As described, most emollients contain hydrocarbon structural elements, which might be expected to adversely affect the performance of diffusion coefficient-enhancing excipients by solubilizing them within the residual non-volatile phase of the vehicle. The formulation generally comprises a cosmetic, cosmeceutical or pharmaceutical active.

Typically the formulation comprises a partition coefficient enhancer selected from the group consisting of the general formula $C_nH_{2n+2}O_2$ where n=3-6 inclusive.

Typically the formulation comprises a hydrocarbyl methylsiloxane emollient compound selected from the group consisting of caprylyl methicone, lauryl methicone, stearyl methicone and caprylyl trimethicone; suitably the hydrocarbyl methylsiloxane emollient is caprylyl methicone.

The formulation may also include a highly volatile solvent selected from the group consisting of hexamethyldisiloxane, octamethyltrisiloxane, ethanol, isopropyl alcohol and water.

Hydrocarbyl Methyl Siloxane Emollient

A limitation of current coenhancer technologies is their inability to incorporate emollients and yet maintain a high degree of saturation of the active and also a high degree of saturation of the diffusion coefficient enhancer, thus overall to ensure optimized skin penetration. It has surprisingly been found that polyol-in-silicone emulsions provide a structural matrix for incorporation of chemically diverse excipients. In particular, the inventors have identified the chemical class of hydrocarbyl methylsiloxane emollient excipients as being of particular interest due to their compatibility with silicone oils.

The formulation of the present invention includes an optionally substituted hydrocarbyl methyl siloxane emollient. The emollients for use in the formulation of the present invention contain hydrocarbon and methyl siloxane backbone structural elements. The methyl siloxane backbone contributes an additional light, smooth, silky, powdery feel to further improve the aesthetics of the resultant formulation. The methyl siloxane backbone may be in the form of a straight chain-, branched- or cyclo-siloxane compound. The hydrocarbyl portion of the emollient compound may be saturated or unsaturated and may include alkyl, alkenyl, alkynyl, haloalkyl, carbocyclyl, for example heterocyclyl, aryl and heteroaryl groups. The hydrocarbyl portion of the emollient compound may be straight chain or branched, and may be substituted or unsubstituted.

According to one embodiment, one or more carbon or silicon atoms of the hydrocarbyl methyl siloxane group may be independently substituted with one or more of the group consisting of small hydrocarbyl group, typically small alkyl group (suitably 1 to 6 carbon atoms), cycloalkyl group, $C_1$ to $_6$ alkoxy, halogen, trifluoromethyl, cyano, thio, amino, nitro, oxo and hydroxyl.

Typically the hydrocarbyl methyl siloxane group is substituted with one or more small alkyl group, halogen group and/or hydroxyl group; generally one or more small alkyl group.

Generally the hydrocarbyl methyl siloxane group is unsubstituted.

The hydrocarbyl methyl siloxane generally has the structure shown below.

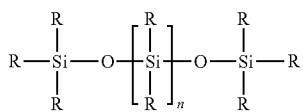

Wherein each R group independently represents a hydrocarbyl group or hydrogen, at least one R group represents methyl, and at least one R group represents a hydrocarbyl group.

Generally 1 to 3 R groups independently represent a hydrocarbyl group comprising 2 or more carbon atoms, typically selected from the group consisting of an alkyl group having a carbon backbone of two or more, an aryl group and an alkyl group attached to an aryl group. Typically the, or each alkyl group is a small alkyl group. Suitably 1 or 2 R groups independently represent a hydrocarbyl group comprising 2 or more carbon atoms.

Typically each R group represents methyl or a hydrocarbyl group comprising 2 or more carbon atoms. Suitably each R group represents methyl, an alkyl group having a carbon backbone of two or more, an aryl group or an alkyl group attached to an aryl group. Typically the, or each alkyl group is a small alkyl group.

According to one embodiment, the hydrocarbyl methyl siloxane refers to compounds having the structure as shown below

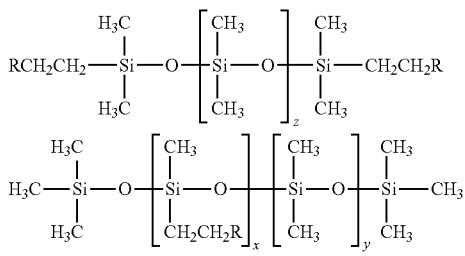

Wherein R represents a hydrocarbyl group, generally an alkyl or aryl group and z, x and y independently represent an integer from 1 to 500.

Particular mention may be made of alkyl methyl siloxanes, aryl methyl siloxanes and alkyl aryl methyl siloxanes. According to one embodiment the emollient is an alkyl methyl siloxane or an alkyl aryl methyl siloxane. Suitable emollients include cetyl dimethicone, stearyl dimethicone, phenyl dimethicone, caprylyl methicone (available, for example, from Dow Corning as TI-2021 AMS), myristyl methicone, stearyl methicone and lauryl methicone (available, for example, from Siltec), caprylyl trimethicone (available, for example from Clariant) and decamethylcyclopentasiloxane.

The dominant chemistry and state of matter of any hydrocarbyl methyl siloxane (including alkyl methyl siloxane and alkyl aryl methyl siloxane) may be estimated from the ratio of hydrocarbon to methyl siloxane and from the chain length of the hydrocarbon. Thus, the principles of selection of appropriate alkyl and alkyl aryl methyl siloxanes are understood by those skilled in the art. Alkyl methyl siloxane and alkyl aryl methyl siloxane which are liquids, by virtue of the lower percentage of hydrocarbon and lower hydrocarbon chain length, are generally preferred as emollients. Such liquid alkyl methyl siloxanes include caprylyl methicone, lauryl methicone, stearyl methicone and caprylyl trimethicone.

Typically the hydrocarbyl methyl siloxane compound has a number average molecular weight of less than 1000, suitably less than 800, generally less than 500. According to one embodiment, the hydrocarbyl methyl siloxane compound has a number average molecular weight of 100 to 700, generally 200 to 400.

Studies on the solubility of actives and functional diffusion coefficient (DC) enhancers may be conducted to select those hydrocarbyl methylsiloxane emollients suitable for use in the current invention. The formulation of the present invention comprises more than one methyl siloxane-containing compound, in particular more than one hydrocarbyl methyl siloxane, typically more than one alkyl-, aryl- or aryl alkyl-methyl siloxane compound (generally having a number average molecular weight of less than 1000).

Generally the hydrocarbyl methyl siloxane consists of or comprises caprylyl methicone.

Suitably the formulation includes one or more cyclomethicone compounds such as cyclopentasiloxane, in particular decamethylcyclopentasiloxane.

FIG. 1 shows the saturated solubility of the corticosteroids fluticasone propionate (FP) and mometasone furoate (MF) in a range of liquid silicones suitable for use in the present invention, including the alkyl methylsiloxane emollient caprylyl methicone, is appropriately low. Thus, even at greatly reduced active doses, a high degree of saturation of the active may be achieved in the non-volatile residual phase in the presence of an emollient.

Diffusion Coefficient-Enhancing Excipients

As described previously, diffusion coefficient-enhancing excipients (DC enhancers) for use in the present invention commonly comprise alcohol, acid or ester derivatives of $C_8$-$C_{22}$ hydrocarbons. The attached FIGS. 2 to 6 show the solubility of straight chain saturated $C_8$-$C_{22}$ alcohol, acid and ester derivatives in various hydrocarbyl methyl siloxanes, 5-NF (decamethylcyclopentacyclooxane) and in the partition coefficient enhancer propylene glycol at 23-25° C.

In the acid and alcohol series, FIG. 2, as carbon chain length increases, solubility in caprylyl methicone decreases to less than 0.1% w/w at $C_{18}$, such that these higher carbon chain lengths may be considered unsuitable for use as the DC enhancer in the formulation of the present invention owing to low solubility-dissolution constraints. Conversely, lower carbon chain length acids and alcohols such as $C_8$ and $C_{10}$ alcohols and $C_8$ and $C_{10}$ acids may be considered to be far too soluble in hydrocarbyl methyl siloxanes including caprylyl methicone, such that their performance as diffusion coefficient-enhancing excipients would be adversely affected. Similarly, long chain (for instance $C_{14}$-$C_{16}$) isopropyl esters are far too soluble in hydrocarbyl methyl siloxanes such as caprylyl methicone to allow performance as DC enhancers. For both of these classes of DC enhancer, up to 50% DC enhancer would be required to be at or near saturation in the non-volatile residual phase. In contrast, the $C_{12}$-$C_{14}$ acids and $C_{12}$ alcohol have appropriate solubility in caprylyl methicone. FIG. 3 shows that $C_{12}$ alcohol has appropriate solubility in a range of hydrocarbyl methylsiloxanes and also in 5-NF (decamethylcyclopentacycloxane).

FIG. 4 shows that the solubility of short chain $C_8$-$C_{10}$ fatty acids and short chain $C_8$-$C_{12}$ fatty alcohols in the partition coefficient (PC) enhancer propylene glycol may be considered too high, such that the performance of such alcohols and fatty acids as DC enhancers would be adversely affected. Conversely, from $C_{16}$-$C_{22}$ solubility is too low to allow adequate performance. Only the $C_{12}$-$C_{14}$ acids and $C_{14}$ alcohol have appropriate solubility in propylene glycol.

FIGS. 5 and 6 plot fatty acid, alcohol and isopropyl ester solubilities in both propylene glycol and caprylyl methicone solvents. As shown in the detail of FIG. 6, only the $C_{12}$-$C_{14}$ acids and $C_{14}$ alcohol have appropriate total solubility in propylene glycol and caprylyl methicone.

As an example of the outline design of a simple co-enhancer system comprising propylene glycol, and, for example, a $C_{14}$ alcohol diffusion coefficient enhancer with caprylyl methicone, we might first consider that the concentration of propylene glycol and caprylyl methicone in the final formulation (otherwise consisting of non-solvents) to be 25% of each. On this basis, the total amount of $C_{14}$ alcohol to saturate both of these phases would be 2.44%/4+2.30%/4=1.185%, approximately 1.2%. Based on experience, concentrations of diffusion coefficient enhancer around the range 1-5% w/w are required, thus in the optimum range for the selected diffusion coefficient enhancers.

The DC enhancers for use in the formulation of the present invention are generally selected from the group consisting of $C_{12}$-$C_{16}$ acids and $C_{12}$-$C_{14}$ alcohols, typically $C_{12}$-$C_{14}$ straight chain fatty acids and $C_{14}$ straight chain primary alcohols. This select group of compounds are suitably soluble in both the hydrocarbyl methyl siloxane and the partition coefficient enhancer, allowing strong diffusion coefficient enhancement and efficient epidermal delivery of the active compound.

The fatty acids for use in the formulation of the present invention have a carbon backbone of 12 to 16 carbon atoms, preferably 12 to 14 carbon atoms. The alcohols for use in the formulation of the present invention have a carbon backbone of 12 to 14 carbon atoms, generally 14 carbon atoms. In some embodiments, the fatty acids/alcohols may comprise substituents from the carbon backbone which may include additional carbon atoms. In particular, the fatty acids/alcohols may comprise hydrocarbyl substituents including 1 to 3 carbon atoms.

Generally the fatty acids/alcohols for use in the formulation of the present invention are not substituted.

The DC enhancer is generally an optionally substituted $C_{12}$-$C_{16}$ fatty acid which may be saturated or unsaturated. Generally the fatty acids/alcohols for use in the formulation of the present invention are saturated.

Typically the DC enhancer is a saturated fatty acid having a carbon backbone of 12 to 14 carbon atoms.

According to one embodiment, the fatty acid/alcohol is unsaturated and the two carbon atoms in the carbon backbone adjacent the/each double bond may be in a cis or trans configuration, generally in a trans configuration.

Alternatively, the DC enhancer may be an optionally substituted $C_{12}$ alcohol which may be saturated or unsaturated. Generally the DC enhancer is a straight chain primary alcohol.

Generally the DC enhancer is a saturated alcohol having a carbon backbone of 12 to 14 carbon atoms, generally 14 carbon atoms. According to one embodiment, the acid or alcohol DC enhancer may be substituted. One or more of the carbon atoms may independently be substituted with one or more $C_1$ to $C_6$ hydrocarbyl group, generally $C_1$ to $C_4$ alkyl group.

Suitable substituted $C_{12}$-$C_{16}$ acids and $C_{12}$-$C_{14}$ alcohols may be readily identified by their combined solubilities in the hydrocarbyl methyl siloxane and the partition coefficient enhancer.

According to one embodiment of the present invention, the DC enhancer is selected from the group consisting of $C_{12}$-$C_{14}$ straight chain fatty acids and $C_{12}$-$C_{14}$ alcohols; in particular the group consisting of $C_{12}$-$C_{14}$ straight chain fatty acids and $C_{14}$ straight chain primary alcohols.

Generally the DC enhancer is selected from the group consisting of lauric acid, myristic acid and myrystyl alcohol.

The amount of DC enhancer required depends on the other components of the formulation, in particular, as described, the identity and amounts of the hydrocarbyl silicone emollient used and the PC enhancer used.

Generally the formulation of the present invention comprises less than about 10% w/w DC enhancer, typically less than about 5% w/w DC enhancer, suitably less than about 4% w/w DC enhancer, generally 1 to 4% w/w. The formulation suitably comprises at least about 0.5% w/w DC enhancer, suitably 0.5 to 2% w/w DC enhancer, typically at least about 0.7% w/w DC enhancer, generally at least about 1% w/w DC enhancer.

Partition Coefficient—Enhancing Excipients

The inclusion of a partition coefficient enhancer (PC enhancer) increases the solubility of the active compound in the stratum corneum barrier and thus increases skin penetration.

The formulation of the invention generally comprises at least one PC enhancer, in particular at least one OH-terminated PC enhancer. Generally the PC enhancer is a primary or secondary alcohol, in particular a diol or polyol compound. In particular the PC enhancer has a structure of the general formula: $C_nH_{2+2}O_2$ where n represents an integer from 3 to 6 inclusive.

Typically the PC enhancer has a number average molecular weight of 1500 or less, typically 750 or less, suitably 150 or less.

Typically the PC enhancer is selected from one or more of the group consisting of (by common name and IUPAC names): propylene glycol, propane-1,2-diol, n=3; butylene glycol, butane-1,3-diol, n=4; pentylene glycol, pentane 1,5 diol, n=5 or hexylene glycol; 2-Methyl-2,4-pentanediol, n=6.

Generally the partition coefficient enhancer is propylene glycol.

Generally a second mutually miscible PC enhancer/co-solvent is present in the formulation to modulate the degree of saturation of the active in the residual phase. This may take the form of a diol, triol, alcohol, ether-alcohol, or alkyl pyrrolidone. Suitable diols are of the general formula $C_nH_{2n+2}O_2$ where n=>6. Suitable alcohols are of the general formula $C_nH_{2n+2}O$, where n=2-3 inclusive. Suitable INCI-listed ether-alcohols are of the general formula $C_nH_{2n+2}O_3$ (n represents an integer from 1 to 10), for example: dipropylene glycol, $C_6H_{14}O_3$; Transcutol (diethylene glycol monoethyl ether), $C_6H_{14}O_3$; butoxydiglycol, $C_8H_{16}O_3$; diethylene glycol, $C_4H_{10}O_3$; dimethoxydiglycol, $C_6H_{14}O_3$ and methoxydiglycol, $C_5H_{12}O_3$. Further suitable INCI-listed ether-alcohols are of the general formula $C_nH_{2n+2}O_2$ (n represents an integer from 1 to 10), for example: butoxyethanol, $C_6H_{14}O_2$; ethoxyethanol, $C_4H_{10}O_2$; ethyl hexanediol, $C_8H_{18}O_2$, methoxyethanol, $C_3H_8O_2$ and methoxyisopropanol, $C_4H_{10}O_2$. A suitable alkyl pyrrolidone is N-methyl pyrrolidone. A suitable triol is glycerol.

In particular, the second mutually miscible PC enhancer/cosolvent may be glycerol or N-methyl pyrrolidone.

FIG. 7 shows the solubility of the corticosteroids fluticasone propionate (FP) and mometasone furoate in a range of water-miscible PC enhancers. FP and MF solubilities vary between the PC enhancers, such that by using blends of the PC enhancers, active solubility in the enhancer residual phase may be adjusted, generally increased, to be at or near drug saturation with active in complete solution.

Similarly, active solubility may be reduced in the non-volatile residual phase. FIG. 8 shows the saturated solubilities of FP and MF in mixtures of propylene glycol:glycerol. As glycerol is added to propylene glycol the solubility of FP and MF decreases. FIG. 9 shows the saturated solubilities of FP and MF in mixtures of propylene glycol:glycerol:water (PG:G:W). As water is added to propylene glycol:glycerol 70:30 the solubility of FP and MF decreases. Water may be present in certain embodiments of the formulation or may be present in the residual phase due to uptake of transepidermal water. Although water is a highly volatile solvent, humectant glycols retain water depending upon ambient conditions.

Table #3 formulations #14-16 contain, respectively, fluticasone propionate, mometasone furoate or retinoic acid at 10% or lower of their usual commercial concentration. Glycerol is added into the propylene glycol dispersed phase to reduce solubility of these actives, thus to increase their degree of saturation in the residual phase.

Table #4 shows formulation examples of the invention where the PC enhancers propylene glycol, pentylene glycol, hexylene glycol and Transcutol are used at 25% w/w as PC enhancers. In examples #17 (propylene glycol, $C_3H_8O_2$) and #18 (pentylene glycol, $C_5H_{12}O_2$) very similar apparent viscosities and spreading behaviours are seen. However, in examples #19 (hexylene glycol, $C_6H_{14}O_2$) and #20 (Transcutol, $C_6H_{14}O_3$) there is a reduction in apparent viscosity. Use of blends of the PC enhancers hexylene glycol, $C_6H_{14}O_2$ and Transcutol, $C_6H_{14}O_3$ with propylene glycol restores apparent viscosity and allows adjustment of drug solubility in the coenhancer residual phase.

The amount of PC enhancer required depends upon the extent of skin penetration enhancement required and on the other components of the formulation, in particular the identity and amounts of the hydrocarbyl silicone emollient used and the DC enhancer used.

Generally the formulation of the present invention comprises less than about 70% w/w PC enhancer, suitably less than about 50% w/w PC enhancer, typically less than about 40% w/w PC enhancer, more suitably less than about 30% w/w PC enhancer. The formulation suitably comprises at least about 10% w/w PC enhancer, typically at least about 20% w/w PC enhancer.

According to one embodiment, the formulation includes 10 to 60% w/w PC enhancer, generally 25 to 45% w/w.

First Dimethicone Macromer Mixture

The first dimethicone macromer mixture includes a dimethicone macromer and a hydrocarbyl methyl siloxane emollient selected from the group consisting of an alkyl methyl siloxane, an aryl methyl siloxane and an alkyl aryl methyl siloxane.

The first dimethicone macromer mixture may include one or more dimethicone macromers.

The first dimethicone macromer mixture generally includes a polyglycol dimethicone macromer. The macromer typically has surfactant properties.

The first dimethicone macromer mixture may include a compound of the following structure:

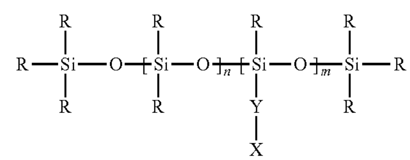

Where R represents H or hydrocarbyl group, in particular C1 to C6 alkyl group;

Y represents a hydrocarbyl group in particular C1 to C6 alkyl group;

X represents an amine, a quaternary amino group or acid functionality.

M and n independently represent an integer from 1 to 50.

The first dimethicone macromer mixture typically includes a dimethicone macromer having a number average molecular weight of more than 1000 (typically more than 2000) and a hydrocarbyl methyl siloxane emollient (generally an alkyl methyl siloxane) having a number average molecular weight of less than 500.

The formulation may include 5 to 45% w/w first dimethicone macromer mixture, typically 10 to 40% w/w, generally 20 to 30% w/w.

The first dimethicone macromer mixture may include 5 to 30% w/w polyglycol dimethicone macromer; generally 10 to 20% w/w; typically 12 to 19% w/w.

Generally the polyglycol dimethicone macromer surfactant comprises one or more polyalkylsiloxane portions (generally one or more dimethylsiloxane portions) and one or more oxypropylene or oxyethylene portions. Suitably the dimethicone macromer may comprise one or more copolymers of ethylene oxide and propylene oxide.

In particular, the first dimethicone macromer mixture includes a polyglycol dimethicone macromer cross-linked with a polyalkylene oxide compound (generally a polyethylene glycol compound, a polypropylene glycol compound or a copolymer of ethylene oxide and propylene oxide).

The first dimethicone macromer mixture may include a polyglycol dimethicone macromer selected from the group consisting of PEG dimethicone PPG crosspolymer and PEG dimethicone bis-isoalkyl PPG crosspolymer.

The first dimethicone macromer mixture may include a polyglycol dimethicone macromer comprising one or more pendant groups from the dimethicone backbone, said pendant group(s) being a polyalkylene oxide group (generally a polyethylene glycol compound, a polypropylene glycol compound or a copolymer of ethylene oxide and propylene oxide). According to one embodiment, the polyglycol dimethicone macromer includes a polyethylene glycol pendant group and a polypropylene glycol pendant group from the dimethicone backbone.

Generally the dimethicone macromer comprises one or more terminal carbinol groups.

The dimethicone macromer may have the structure of a dihydroxy terminated block copolymer oxyethylene-dimethylsiloxane-oxyethylene; oxypropylene-dimethylsiloxane-oxypropylene or caprolactone-dimethylsiloxane-caprolactone of different molecular weights containing different weight % of non-siloxane units. Optionally such block co-polymers may include pendant oxyalkylene groups. Typically the block copolymer may be cross-linked.

The dimethicone macromer may have a non-siloxane content of 20 to 70 wt. %.

The number average molecular weight of the, or each dimethicone macromer is generally 800 or more, suitably 1000 or more, typically 1000 to 10000, suitably 2000 to 7000.

According to one embodiment, the greater the number average molecular weight of the dimethicone macromer, the greater the non-siloxane weight percentage content.

The dimethicone macromer may be in the form of a dimethicone-containing central linking group, linked to two to five polyoxyalkylene groups, generally two to five and oxypropylene. Generally the pendant polyoxyalkylene groups include 5 to 50 repeat units, suitably 10 to 30 repeat units, typically 15 to 20 repeal units.

Typically the dimethicone macromer surfactant comprises a dimethicone backbone with one or more pendant oxyethylene groups and one or more pendant oxypropylene groups.

For example, the dimethicone macromer may have the general structure below of the pendant polymer PEG/PPG-18/18 Dimethicone where m and n independently represent pendant block copolymers of oxyethylene and oxypropylene. For example, the dimethicone macromer may have the general structure below where m and n independently represent an integer from 10 to 30, suitably wherein in =20 and n=15. Such macromers are commercially available under the registered trade mark Silsoft® SF1540.

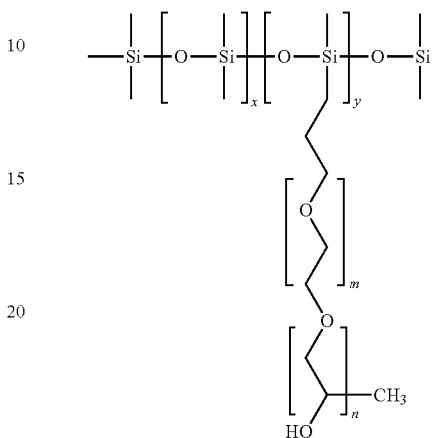

Where x and y independently represent an integer from 1 to 500.

Alternatively or additionally, the dimethicone macromer may comprise a dimethicone backbone with one or more oxyethylene end blocks, generally one or more PEG end blocks, typically two PEG end blocks. For example, the structure of an end-block copolymer, bis-PEG-10 Dimethicone is shown below, where x is an integer from 1 to 500.

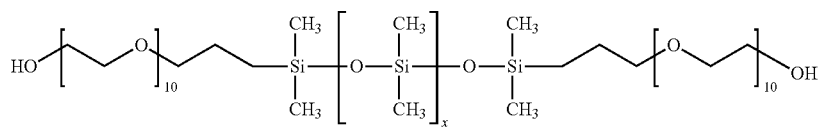

an integer from 10 to 30, suitably 18, x-o and y independently represent an integer from 1 to 500, and o represents an integer from 1 to 100.

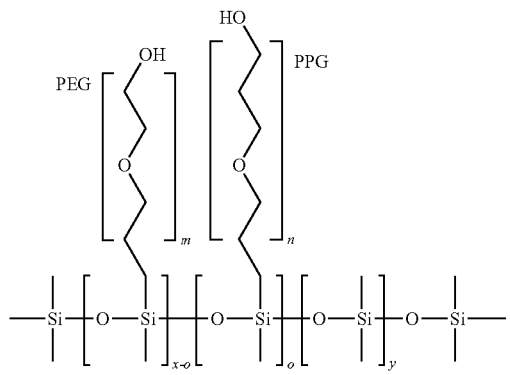

Alternatively or additionally, the dimethicone macromer may comprise a dimethicone backbone with one or more Advantageously, the dimethicone macromer is cross-linked. In particular, a first dimethicone backbone is cross-linked with a second dimethicone backbone through one or more cross linking groups, for example substituted or unsubstituted hydrocarbyl groups, in particular substituted or unsubstituted alkylene groups. In particular, the cross linking groups may be selected from the group consisting of unsubstituted alkylene groups and oxyalkylene groups, in particular one or more oxyethylene or one or more oxypropylene groups. Generally the oxyalkylene cross-linking group includes 5 to 50 repeat groups. The dimethicone macromer may also include one or more pendant oxyalkylene groups which do not cross-link the dimethicone backbones.

Dimethicone PEG-10 crosspolymer is an example of a polyethylene glycol cross-linked dimethicone macromere, where y and z independently represent an integer from 1 to 500.

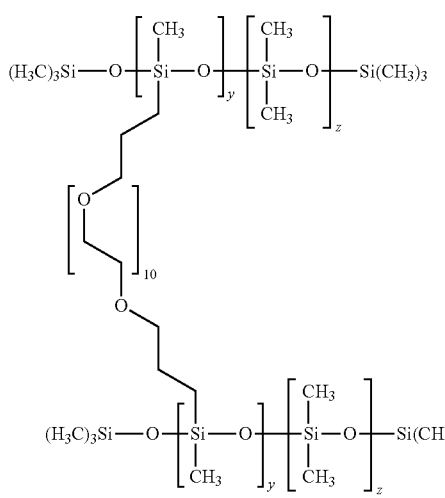

PEG-12 dimethicone crosspolymer is an example of a hydrocarbon diene cross-linked copolymer emulsifier with pendant polyethylene glycol groups, where x, y and z independently represent an integer from 1 to 500.

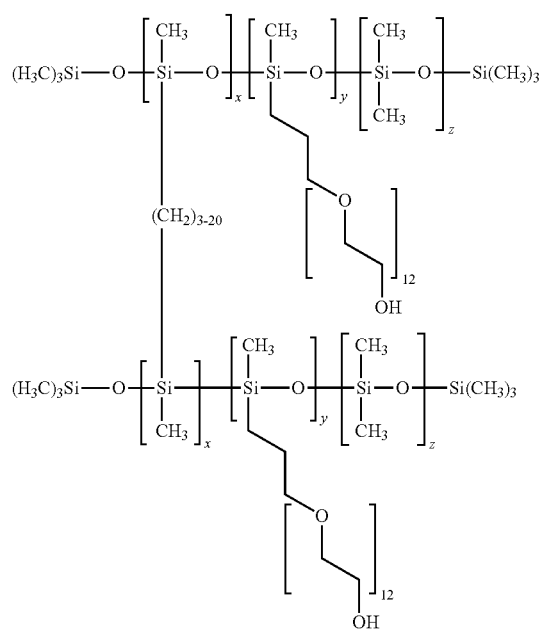

According to one embodiment, the dimethicone copolymer comprises a first dimethicone backbone including at least one pendant group comprising oxyalkylene (in particular oxypropylene or oxyethylene group), cross-linked with a second dimethicone backbone including at least one pendant group comprising oxyalkylene (in particular oxypropylene or oxyethylene group), wherein the cross-linking group comprises an oxyalkylene group (in particular oxypropylene or oxyethylene group). The repeating oxyalkylene group may be linked to the, or each dimethicone backbone through a substituted or unsubstituted hydrocarbyl group, in particular a substituted or unsubstituted alkyl group (generally $C_{1-4}$ alkyl group).

Generally the pendant group(s) is an oxyethylene group, typically including 5 to 50 repeat groups, generally 10 to 15 repeat groups.

Typically the cross-linking group is an oxypropylene group, typically including 5 to 50 repeat groups, generally 15 to 30 repeat groups.

PEG-12 dimethicone PPG 20 crosspolymer is an example of a suitable silicone polyether for use as the dimethicone macromer. with a polypropylene glycol crosslink and pendant polyethylene glycol, where x, y and z independently represent an integer from 1 to 500.

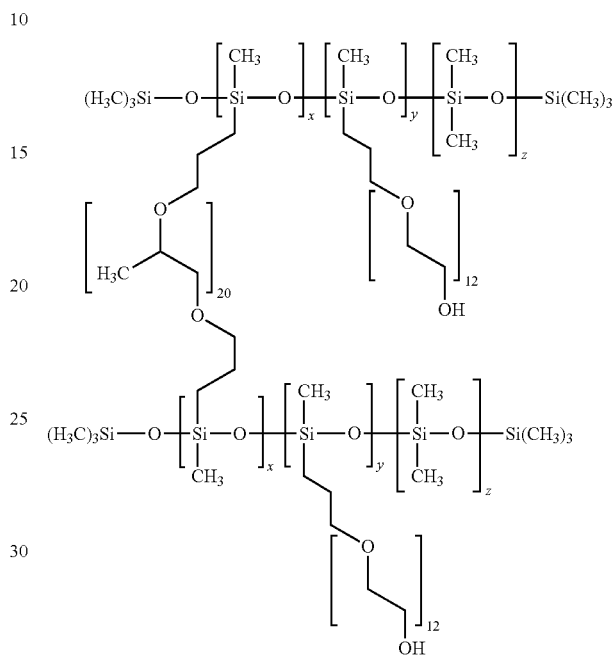

A further example of a suitable cross-linked silicone polyether is provided below, where x, y and z independently represent an integer from 1 to 500:

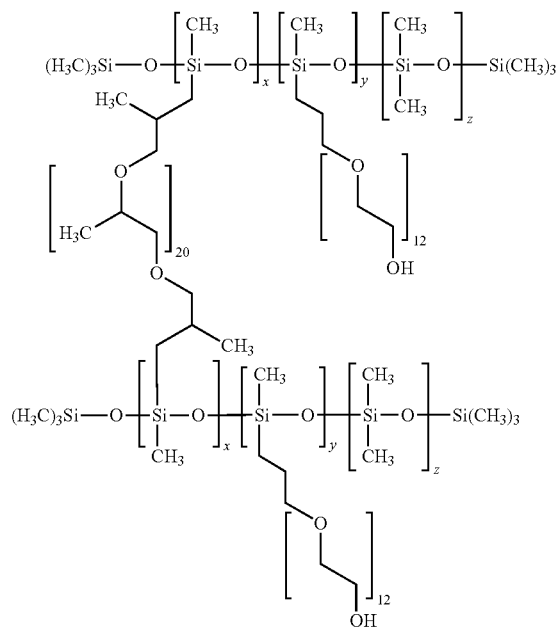

These PPG crosslinked PEG-12 pendant dimethicone crosspolymers are particularly useful in stabilizing propylene glycol in silicone oil non-aqueous emulsions containing dissolved $C_{12}$-$C_{14}$ acid and $C_{12}$ alcohol functional excipients.

Alternatively or additionally, the dimethicone macromer may comprise a dimethicone backbone with an ionic pendant chain of the general structure as shown below where X may be a hydrophilic amine, quaternary amino or acid functional grouping, and n and m independently represent an integer from 1 to 500.

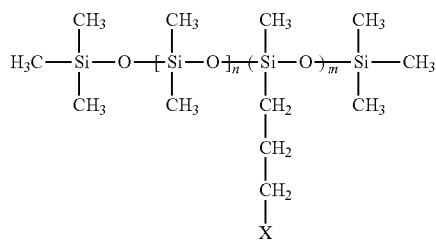

Especially preferred is a pyrrolidone carboxylic acid functionalized dimethicone macromer, in particular that with INCI name PCA dimethicone, This ionic dimethicone macromer, especially in combination with PPG crosslinked PEG-12 pendant dimethicone crosspolymers is particularly useful in stabilizing propylene glycol in silicone oil non-aqueous emulsions containing dissolved $C_{12}$-$C_{14}$ acid and $C_{12}$ alcohol functional excipients, where m and n independently represent an integer from 1 to 500.

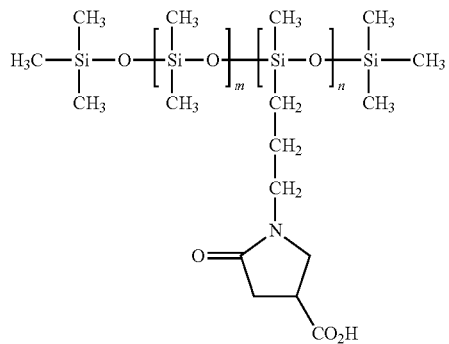

According to one embodiment the first dimethicone macromere mixture of the formulation of the present invention comprises more than one dimethicone macromer, generally more than one polydialkylsiloxane diol compound or ionic dimethicone macromer surfactant.

Generally the dimethicone macromer(s) is dispersed, dissolved or suspended in the hydrocarbyl methyl siloxane compound(s) or vice versa.

In particular, the, or one of, the dimethicone macromers may be dispersed, dissolved or suspended in an alkyl methyl siloxane such as caprylyl methicone, lauryl methicone, stearyl methicone or caprylyl trimethicone.

Alternatively or additionally, the, or one of the dimethicone macromers may be dispersed, dissolved or suspended in a methyl siloxane compound, such as a cyclomethicone such as decamethylcyclopentasiloxane.

According to one embodiment, the formulation of the present invention comprises more than one siloxane-containing compound, in particular one or more alkyl-methyl siloxane, aryl-methyl siloxane and/or alkyl aryl-methyl siloxane compound(s) (generally having a number average molecular weight of less than 1000) and one or more dimethicone macromer(s) (typically having a number average molecular weight of more than 1000, suitably more than 2000), generally more than one polyalkylsiloxane diol compounds.

Generally the formulation comprises a mixture of one or more alkyl methyl siloxane compound and/or alkyl aryl methyl siloxane compound(s) (generally having a number average molecular weight of less than 1000) and one or more dimethicone macromer(s) having a number average molecular weight of more than 1000, wherein the mixture comprises 50 to 95% w/w alkyl and/or alkyl aryl methyl siloxane compound(s) having a number average molecular weight of less than 1000, and 5 to 50% w/w dimethicone macromer surfactant.

According to one embodiment, there is provided a formulation comprising a hydrocarbyl methyl siloxane compound, an alkyl siloxane compound (generally a methyl siloxane compound, in particular a cyclomethicone compound), and two polyalkylsiloxane macromers.

The formulation of the present invention may comprise one or more alkyl-methyl siloxane, aryl-methyl siloxane or alkyl aryl-methyl siloxane compounds, typically selected from the group consisting of caprylyl methicone, lauryl methicone, stearyl methicone, caprylyl trimethicone and decamethylcyclopentasiloxane; and one or more dimethicone macromers, generally comprising one or more polyalkylsiloxane portions (generally one or more dimethylsiloxane portions) and one or more oxypropylene or oxyethylene portions. Typically the dimethicone macromer comprises one or more copolymers of ethylene oxide and propylene oxide.

According to one embodiment, the formulation of the present invention comprises an alkyl methyl siloxane and/or an aryl alkyl methyl siloxane having a number average molecular weight of 800 or less and a cross-linked dimethicone macromer having a number average molecular weight of more than 1000, said dimethicone macromer comprising one or more copolymers of ethylene oxide and propylene oxide.

Generally the viscosity of the mixture of hydrocarbyl methyl siloxane compound and dimethicone macromer is greater than 200,000 cSt, typically 250,000, to 1,000,000 cSt.

The first dimethicone macromer mixture may comprise a mixture of caprylyl methicone and a polyethylene glycol dimethicone/polypropylene glycol cross-linked polymer. Suitable compositions are available from Dow Corning® under the INCI name caprylyl methicone PEG-12 dimethicone/PPG-20 cross polymer (EL-7040 hydro elastomer blend).

The formulation of the present invention may comprise a mixture of an alkyl methyl siloxane (generally having a number average molecular weight of less than 1000, typically less than 400) and a polyalkylsiloxane diol compound.

Second Dimethicone Macromer Mixture

The formulation of the present invention comprises a second dimethicone macromer mixture including a methyl siloxane compound and a cross-linked dimethicone macromer.

The formulation of the present invention may comprise a mixture of an alkyl siloxane compound generally having a number average molecular weight of less than 1000 (typically a cyclomethicone compound, in particular an alkyl cyclomethicone compound) and a dimethicone macromer having a number average molecular weight of more than 1000, typically a cross-linked polyalkylsiloxane diol. Suitable compositions are available from Dow Corning® under the trade name ST Elastomer 10.

First and Second Dimethicone Macromer Mixtures

According to one embodiment, the formulation of the present invention may comprise a first dimethicone macromer mixture including a hydrocarbyl methyl siloxane compound (generally an alkyl methyl siloxane or alkyl aryl methyl siloxane) and a polyglycol dimethicone macromer, typically a cross-linked polyalkylsiloxane diol compound; and a second dimethicone macromer mixture including a methyl siloxane compound (in particular a methyl cyclomethicone compound) and a dimethicone macromer, typically a cross-linked polyalkylsiloxane diol compound.

According to one embodiment, the formulation of the present invention comprises 50% w/w or less hydrocarbyl methyl siloxane, typically 10 to 40% w/w hydrocarbyl methyl siloxane, suitably 20 to 30% w/w hydrocarbyl methyl siloxane.

According to one embodiment, the formulation comprises less than 40% w/w of any alkyl siloxane-containing compound, generally 20% w/w or less, suitably 20% w/w or less.

The formulation of the present invention may comprise 30% w/w or less dimethicone macromer, in particular cross-linked polyalkylsiloxane diol compound.

According to one embodiment, the formulation of the present invention comprises 30% w/w or less hydrocarbyl methyl siloxane having a number average molecular weight of 1000 or less, generally one or more alkyl methyl siloxane or alkyl aryl methyl siloxane compound; typically 20% w/w or less; suitably 10% w/w or less.

According to one embodiment, the formulation of the present invention comprises 30% w/w or less dimethicone macromer surfactant having a number average molecular weight of more than 1000, generally more than 2000; typically 20% w/w or less; suitably 10% w/w or less.

According to one embodiment, the second dimethicone macromer mixture includes a methyl siloxane compound having a number average molecular weight of less than 1000 and a cross-linked polyalkylsiloxane diol dimethicone macromer having a number average molecular weight of more than 1000, generally of more than 2000. In particular, the second dimethicone macromer mixture may include 5 to 30% w/w cross-linked dimethicone macromer; generally 10 to 20% w/w; typically 12 to 19% w/w.

The formulation may comprise 5 to 45% w/w second dimethicone macromer mixture, typically 10 to 40% w/w, generally 20 to 30% w/w.

Generally the first and second dimethicone macromers are mixed in a ratio of from 3:1 to 0.6:1, ideally 1.5:1.

The first cross-linked polyalkylsiloxane diol compound may be in the form of a mixture comprising an alkyl or alkyl aryl methyl siloxane and a dimethicone macromer, the second cross-linked polyalkylsiloxane diol may be in the form of a mixture comprising an alkyl siloxane compound, such as an alkyl cyclomethicone compound and a dimethicone macromer.

According to one embodiment, the first cross-linked polyalkylsiloxane diol compound may be a PEG dimethicone/PPG crosspolymer such as that sold under the trade name Dow Corning EL-7040 Hydro Elastomer Blend comprising 17.5-19.50% of PEG-12 dimethicone/PPG-20 crosspolymer.

Typically the second dimethicone macromer mixture comprises a dimethicone cross-linked polymer swelled in a silicone fluid such as, for instance, cyclopentasiloxane such dimethicone macromer mixtures tend to impart a dry smoothness and a non-greasy feel to the skin. In thickening the continuous phase of water-in-silicone or polyol in silicone emulsions they improve physical stability and help reduce creaming and phase separation. The second cross-linked polyalkylsiloxane diol compound may be in the form of a mixture of cylcopentacyloxane and dimethicone cross polymer such as that sold under the trade name Dow Corning ST Elastomer 10 comprises 12.5% high molecular weight silicone elastomer in decamethylcyclopentasiloxane.

Formulation

According to one aspect of the present invention the formulation as described herein may be mixed with solvents, carriers and other excipients to form a pharmaceutical, cosmetic or cosmeceutical composition. The composition is generally in the form of a cream, serum, gel, solution, suspension or dispersion, including a skincare or haircare product such as a shampoo or conditioner.

The formulation may be mixed with solvents including water, and optionally alcohol, in balance to ensure physical stability.

Alternatively, the formulation of the present invention may comprise less than 1% w/w alcohol. This embodiment can be associated with important advantages as the inclusion of alcohol can be associated with drying of skin.

In some applications, for example in the treatment of hair condition, or where a clear appearance is required or where moisturising or more medical product perception is required it may be appropriate to formulate these technologies to include water and alcohol. Table #6 shows examples of Gel-Serum formulations. Column #2-4 of Table #6 shows typical gel-serum formulation, in which the volatile hexamethyldisiloxane (Dow Corning Q7-9180 silicone fluid 0.65 cSt) has been replaced with 25% ethanol:water. Gel-serum #1-3 are clear gel-serum which are cooling, soft and spreads easily on the skin, are non greasy and non tacky and are readily absorbed. Skin feel after application is light, silky and smooth.

In one embodiment, the composition of the invention further comprises one or more UV blockers or UV absorbers. A UV absorber may be, for example, a strong UV absorber that exhibits relatively high absorption values in the UV-A range of about 320-380 nanometers, but is relatively transparent above about 380 nm.

Process for Manufacture

Generally the active agent and the DC functional excipient are presented in solution during manufacture, typically totally in solution. Additionally, it is believed that the combination of the two silicone macromers as described (for example as in EL-7040 and ST Elastomer-10) increase the physical stability of the PC functional enhancer. For this reason a silicone macromer PC enhancer premix may be prepared before the volatile solvents are added.

Outline Suitable Process: Single Vessel Manufacture weigh out into suitable container and record weight of DC enhancer(s)

weigh out into container and record weight of PC enhancer(s) and cosolvents heat gently to 30-35 C to dissolve DC enhancer(s) if required weigh out into container and record weight of active agent(s)

heat gently to 30-35 C to ensure active agent(s) are totally in solution weigh out into container and record weight of dimethicone copolyol emulsifier weigh out into container and record weight of silicone elastomer blend mix with a blade until "dough ball" structure is obtained weigh out into container and record weight of volatile solvent(s)
    methyl siloxane (Cream formulations)
    water and ethanol (Gel-type formulation)
mix to homogeneity
pack A 50 g batch of placebo formulation was made according to the manufacturing process above.

| Material | 50 g Formulation #1 16/02/15 paper | Formulation #1 actual |
|---|---|---|
| Drug | — | — |
| Propylene glycol | 12.5 | 12.5339 |
| Glycerol | 3.125 | 3.1315 |
| Myristyl alcohol (1) | 0.3 | 0.5005 (1 + 2) |
| ST Elastomer | 12.5 | 12.4905 |
| EL-7040 | 11.35 | 11.3544 |
| Myristyl alcohol (2) | 0.2 | — |
| 0.65 | 10 | 10.0059 |
| Total | 49.975 | 50.0167 |
| Comments Code/details | | 50 g Formulation #1 16/02/15 pump pack |

The images shown in FIG. 10 demonstrate the in-process appearance:
FIG. 10A after addition of both polymers
FIG. 10B after mixing to form the "dough ball"
FIG. 10C after addition of the volatile hexamethyldisiloxane and final mixing Outline Suitable Process: Two-Vessel Manufacture (with Premix)
Premix:
A premix of propylene glycol-glycerol-NaCl was made 32:7.50:0.50, thus approximately 1.25% NaCl.
Vessel #1
    PG:G:NaCl (1.25%)+Malc (1+2)+Active; heat to dissolve <60° C., cool to 50° C.
Vessel #2
    EL-7040+0.65 Turrax T25 RED zone for 5 minutes to give thick homogenous gel
    Add contents of vessel #1 to vessel #2 over 5 minutes Turrax T25 BLACK zone for 7 minutes with constant movement of the high shear head around vessel #2.
    Add ST-E, mix by large spatula for 2 minutes; sonicate for a further 3 minutes. Record viscosity and pack.

| Material | % w/w Serum #2 07/12/15 paper (P) 100 g scale | % w/w Serum #2 07/12/15 actual 100 g scale | % w/w Serum #3 07/12/15 paper (P) 100 g scale | % w/w Serum #3 07/12/15 actual 100 g scale |
|---|---|---|---|---|
| Active | 0.50 | 0.5012 | 1.00 | 1.0000 |
| Myristyl alcohol (1 + 2) | 1.50 | 1.5010 | 1.50 | 1.5020 |
| Stock PG:G NaCl 1.25% | 40.00 | 40.0137 | 40.00 | 40.0059 |
| EL-7040 | 24.00 | 24.01 | 24.00 | 24.05 |
| ST Elastomer | 14.00 | 14.05 | 13.50 | 13.57 |
| 0.65 | 20.00 | 20.03 | 20.00 | 20.01 |
| total | 100.00 | | 100.00 | |
| viscosity (NDJ-4A) | | 78@ 0.3 rpm spindle #4 | | 78@ 0.3 rpm spindle #4 |

Active Compounds

Suitably, the active compound(s) for inclusion in the formulations described herein is selected from retinoids, retinoic acid metabolic blocking agents (RAMBAs), alpha and beta hydroxy acids and polymers and derivatives thereof, immune response modifier compounds, vitamin D analogues, corticosteroids, anti-rosacea, agents, antihistamines, antibacterial agents, antiacne agents, antifungal agents, antiviral agents, cytotoxic agents, psoralens, antialopecia agents, anti-androgens, anti-pruritic agents, keratolytic agents, skin lightening and depigmenting agents, dithranol, antiseptics, anaesthetics, analgesics, neuropathics, non-steroidal anti-inflammatory agents, vasoactive agents and agents to combat dry and ageing skin. In one embodiment, the formulation may comprise more than one pharmaceutically active compound, salt or derivative thereof. Suitable concentration ranges for the active compound(s) range from about 0.001% to about 10% by weight of the formulation depending on the nature of the active compound or combination of active compounds.

In one embodiment, the pharmaceutically active compound is a retinoid. Examples of suitable retinoids include, but are not limited to, tazarotene, tretinoin, isotretinoin, acitretin, etretinate, adapalene, bexarotene, alitretinoin, retinol, retinal, retinyl palmitate, retinyl acetate, retinyl propionate, retinyl linoleate, ethyl 5-(2-(4,4-dimethylthiochroman-6-yl)ethynyl)thiophene-2-carboxylate, 6-(2-(4,4-dimethylthiochroman-6-yl)-ethynyl)-3-pyridylmethanol and 6-(2-(4,4-dimethylthiochroman-6-yl)-ethynyl) pyridine-3-carbaldehyde, salts thereof, derivatives thereof and mixtures thereof. In one embodiment, the retinoid is tazarotene. In an alternative embodiment, the retinoid is tretinoin. In an alternative embodiment, the retinoid is retinol. In another embodiment, the formulation comprises a retinoid in combination with a second pharmaceutically active compound. In one embodiment the combination is tazarotene and a second pharmaceutically active compound. In another embodiment the combination is tretinoin and a second pharmaceutically active compound.

Suitably, one combination of the retinoid is with a corticosteroid, such as clobetasol propionate; or in combination with a vitamin D analogue such as calcipotriene; or in combination with an antibacterial such as clindamycin or a pharmaceutically acceptable salt thereof (e.g. clindamycin phosphate). Alternatively, in an embodiment, the present formulations comprise tretinoin in combination with an antibacterial agent, such as clindamycin or a pharmaceutically acceptable salt thereof (e.g. clindamycin phosphate).

Suitable concentration ranges for the retinoid in the formulation include, for example, about 0.001% to about 1% by weight of the formulation. In one embodiment the retinoid is present in an amount from about 0.01% to about 1% by weight. In another embodiment the retinoid is present in an amount from about 0.025% to about 0.5% by weight. In another embodiment the retinoid is present in an amount from about 0.005% to about 0.025% by weight. In one embodiment when the retinoid is tazarotene, it is present in an amount from about 0.05% or 0.1% by weight. In another embodiment when the retinoid is tretinoin, it is present in an amount from about 0.005%, 0.025%, 0.05% or 0.1% by weight. In another embodiment when the retinoid is retinol, it is present in an amount from about 0.05% or 0.1% or 1.0% by weight.

A suitable retinoic acid metabolic blocking agent (RAMBA) for use herein as a pharmaceutically acceptable active compound is Talarozole.

In another embodiment alpha and beta hydroxy acids and polymers and derivatives thereof: alkyl hydroxycarboxylic acids, aralkyl and aryl 2-hydroxycarboxylic acids, polyhydroxy-carboxylic acids, hydroxy-polycarboxylic acids.

2-hydroxycarboxylic acids present in forms other than the acid, such as, for example, salts or lactones; typical lactone forms include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone; 2-ketoacids present as a free acid or an ester form, or in a salt form with an organic base or an inorganic alkali; representative 2-ketocarboxylic acids and their esters: ascorbic acid, quinic acid, isocitric acid, tropic acid (2-phenyl 3-hydroxypropanoic acid), trethocanic acid, 3-chlorolactic acid, citramalic acid, agaricic acid, aleuritic acid, pantoic acid, lactobionic acid and hexulosonic acid.

Suitable immune response modifier compounds, immunosuppressant agents, immunoregulating agents and immunomodulators for use herein include chemically or biologically-derived agents that modify the immune response or the functioning of the immune system (by the stimulation of antibody formation or the inhibition of white blood cell activity). Exemplary agents or compounds include, but are not limited to cyclic peptides (such as cyclosporine), tacrolimus, tresperimus, pimecrolimus, sirolimius (rapamycin), verolimus, laflunimus, laquinimod, mycophenolic acid, and imidazoquinoline amines such as imiquimod, salts thereof, derivatives thereof, and mixtures thereof.

Suitable vitamin D analogues include, but are not limited to, calcidiol, calcitriol, calcipotriene, paricalcitol, 22-oxacolcitriol, dihydrotachysterol, calciferol, salts thereof, derivatives thereof, and mixtures thereof.

Suitable corticosteroids include, but are not limited to, alclometasone dipropionate, amcinonide, beclomethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, prednicarbate, salts thereof, derivatives thereof, and mixtures thereof.

Combinations of vitamin D analogues and corticosteroids, for example fluticasone propionate or mometasone furoate in combination with calcipotriene are suitable.

Suitable anti-rosacea compound include, but are not limited to, clindamycin, erythromycin, metronidazole and azelaic acid.

Suitable antihistamines include, but are not limited to, cetirizine, vapitadine, diphenhydramine, triprolidine, pyrilamine, chlorcyclizine, promethazine, carbinoxamine, tripelennamine, brompheniramine, hydroxyzine, terfenadine, chlorpheniramine, salts thereof, derivatives thereof, and mixtures thereof.

Suitable antibacterial agents include, but are not limited to, gentamycin, neomycin, streptomycin, cefpodoxime proxetil, clindamycin, lincomycin, erythromycin, bacitracin, gramicidin(s), vancomycin, doxycycline, minocycline, oxytetracycline, tetracycline, fosfomycin, fusidic acid, mupirocin, sulfacetamide, metronidazole and dapsone, salts thereof, derivatives thereof, and mixtures thereof.

Suitable antifungal agents include, but are not limited to, those selected from the group consisting of echinocandins such as anidulafunin, caspofungin and micafungin; polyenes such as amphotericin B, candicidin, filipin, fungichromin, hachimycin, hamycin, lucensomycin, mepartricin, natamycin, nystatin, pecilocin, perimycin; allylamines such as butenafine, naftifine and terbinafine; imidazoles such as bifonazole, butoconazole, chlormidazole, cloconazole, clotrimazole, econazole, enilconazole, fenticonazole, flutrimazole, isoconazole, ketoconazole, lanoconazole, miconazole, neticonazole, omoconazole, oxiconazole nitrate, sertaconazole, sulconazole and tioconazole; thiocarbamates such as liranaftate, tolciclate, tolindate and tolnafate; triazoles such as albaconazole, fluconazole, itraconazole, posaconazole, ravuconazole, saperconazole, terconazole and voriconazOle; and other antifungal agents such as acrisorcin, amorolfine, biphenamine, bromosalicylchloranilide, buclosamide, calcium propionate, chlorphenesin, ciclopirox, cloxyquin, coparaffinate, exalamide, flucytosine, haloprogin, hexetidine, loflucarban, nifuratel, potassium iodide, propionic acid, pyrithione, salicylanilide, sodium propionate, sulbentine, tenonitrozole, triacetin, undecylenic acid, zinc propionate, griseofulvin, oligomycins, pyrrolnitrin, siccanin, viridian, salts thereof, derivatives thereof, and mixtures thereof.

Suitable antivirals include, but are not limited to, acyclovir, desciclovir, carbovir, famciclovir, foscarnet sodium, ganciclovir, interferons, penciclovir, valaciclovir, salts thereof, derivatives thereof, and mixtures thereof.

Suitable cytotoxic agents include, but are not limited to, azathioprine, cyclophosphamide, cyclosporine, methotrexate, hydroxyurea, thalidomide, bleomycin, fluorouracil, salts thereof, derivatives thereof, and mixtures thereof.

An exemplary psoralen is methoxsalen. An exemplary anti-alopecia agent is minoxidil.

Suitable anti-androgens include, but are not limited to, spironolactone, cyproterone, flutamide, finasteride, salts thereof, derivatives thereof, and mixtures thereof.

Suitable anti-pruritics include, but are not limited to, calamine, camphor and menthol, derivatives thereof, and mixtures thereof. Other suitable anti-pruritics include kappa opioid agonists, protease inhibitors and the PAR-2 inhibitors.

Suitable keratolytic agents, for example for use in the treatment of acne include, but are not limited to, benzoyl peroxide, salicylic acid, urea, resorcinol, sulphur, salts thereof, derivatives thereof, and mixtures thereof.

Suitable antiseptics include, but are not limited to chlorhexidine, cetrimide, povidone iodine, triclosan, salts thereof, derivatives thereof, and mixtures thereof. Suitable anaesthetics and analgesics include, but are not limited to, benzocaine, lidocaine, prilocaine and choline salicylate, salts thereof, derivatives thereof, and mixtures thereof.

Suitable nonsteroidal anti-inflammatory agents include, but are not limited to, diclofenac, ibuprofen, ketorolac and ketoprofen and their optical isomers, salicylate esters including methyl salicylate and associated agents such as menthol, camphor, capsaicin and the like. Suitable nonsteroidal anti-inflammatory agents with specificity for COX-2 over COX-1 include but are not limited to, celecoxib and refecoxib.

Suitable vasoactive agents include, but are not limited to glyceryl trinitrate, Alprostadil and the like.

Suitable agents for treatment of dry and ageing skin include lactic acid, glycolic acid and lactobionic acid.

The formulation of the present invention is generally in the form of a cream, gel, paste, solution, suspension, dispersion, emulsion, foam or ointment.

According to one embodiment, the formulation of the present invention is in the form of a serum or gel-serum.

According to one embodiment, the formulation of the present invention is in the form of a cream. Alternatively, the formulation of the present invention may be in the form of an emulsion. Where the formulation is an emulsion, polymers, particles and co-emulsifiers may be included to improve physical stability.

The active compounds and other ingredients may form suspensions, solutions, or emulsions in suitable oily or aqueous vehicles, and may contain formulatory agents such as suspending, stabilizing and/or dispersing agents. It is possible to add, if necessary, an adjuvant chosen from antioxidants, surfactants, other preservatives, film-forming, keratolytic or comedolytic agents, perfumes, flavorings and colourings.

The formulation of the present invention generally comprises less than 50 vol. % water, typically less than 10 vol. %, generally less than 0.05 vol. % water. According to one embodiment, the composition of the present invention does not comprise water.

The formulation of the present invention is generally self preserving, and is typically sterile. The sterile media employed in the preparation of suitable formulations are all readily obtainable by standard techniques well-known to those skilled in the art.

Forms chiefly conditioned for application to biological membranes may take the form, for example, of creams, milks, gels, dispersions or, lotions thickened to a greater or lesser extent, aerosol formulations (e.g. sprays or foams) or lotions. Other conventional forms for this purpose include serums, creams, emulsions, lotions, pastes, sprays, and aerosols.

The composition of the present invention may comprise an aqueous or non-aqueous base also comprising one or more dispersing agents, solubilising agents or suspending agents. Liquid sprays can be pumped, or are conveniently delivered from pressurized packs. Drops can be delivered via a simple dropper-capped bottle, via a plastic bottle adapted to deliver liquid contents drop-wise, or via a specially shaped closure.

Ointments and creams may, for example, be formulated with an aqueous or non-aqueous base with the addition of suitable thickening and/or gelling agents. Lotions may be formulated with an aqueous or non-aqueous base and will in general also contain one or more emulsifying agents, stabilizing agents, dispersing agents, suspending agents, thickening agents, or colouring agents.

The percentage by weight of a therapeutic agent of the invention present in the topical formulation will depend on various factors, but generally will be from 0.005% to 10% of the total weight of the formulation, and typically 0.1-5% by weight.

The active compounds mentioned in this specification can exist in different forms, such as free acids, free bases, esters and other prodrugs, salts and tautomers, for example, and the invention includes all variant forms of the agents.

There is also provided the product described above for therapeutic use.

Method of Treatment

According to an aspect of the present invention there is provided a method of preventing, reducing the likelihood of, alleviating or treating a medical condition in the human or animal body comprising the topical administration in a therapeutically effective amount of the formulation described herein.

According to a further aspect of the present invention, there is provided the formulation as described herein for use in the prevention, alleviation or treatment of a medical condition of the human or animal body.

Generally the methods/uses of the present invention provide topical relief of the medical condition for at least 4 hours after administration of the composition, typically at least 6 hours, suitably at least 12 hours after administration.

As the formulation of the present invention is administered topically, the effects are generally associated with a rapid onset. Generally the formulation provides topical relief from the medical condition within 15 minutes or less of application, typically within 10 minutes or less, suitably within 5 minutes or less of application.

Generally the topical relief effects have a duration of 4-6 hours, typically at least 12 hours.

The method involves the topical application of the formulation to the area affected by the condition or disorder, and to surrounding tissue. Topical application of the formulation improves the bioavailability of the pharmaceutical actives contained therein, making dosing more predictable and reducing the likelihood of any adverse reaction.

The methods and uses of the present invention are generally topical and the method of the present invention typically provides a focused method of exploiting the beneficial effects of the active compound(s) whilst limiting the associated dosage required and the risk of adverse effects.

The methods/uses of the present invention generally involve the application of the formulation to the skin or mucous membrane(s) of the patient. According to one embodiment, the methods/uses may involve the application of the formulation to the genitals of the patient.

The medical condition may be selected from the group consisting of conditions associated with or, caused by one or more of pain and/or inflammation, pruritus, acne, eczema, psoriasis, rosacea, nappy rash, dry skin, microbial conditions including fungal and/or bacterial conditions such as skin infections including yeast infections and dermatophyte infections, dry or ageing skin, sun spots and alopecia.

Suitable skin conditions for treatment with the formulation of the present invention include vitiligo, eczema, psoriasis and skin problems related to certain lymphomas.

The method of the present invention may include the application of UV light to the affected area.

The medical condition may be a viral, fungal and/or bacterial condition.

The medical condition may be partly or wholly caused by or associated with a local immune response, in particular involving a histamine, wherein the formulation comprises one or more antihistamines, immunosuppressant agents, immunoregulating agents and/or immunomodulators.

According to one embodiment, the method promotes the growth and repair of body tissues and includes the application of the formulation comprising one or more steroid compounds, in particular one or more corticosteroid compounds.

The medical condition may be partly or wholly caused by or associated with a vitamin D deficiency.

According to one embodiment, the method treats, mitigates or prevents the formation of wrinkles, acne or psoriasis and includes the application of the formulation comprising one or more of the group consisting of retinoid compounds, retinoic acid metabolic blocking agents (RAMBAs), alpha and beta hydroxy acids and polymers and derivatives thereof.

According to one embodiment, the formulation comprises one or more analgesic or anti-inflammatory compounds and the condition is associated with topical and/or inflammation.

The medical condition is generally treated via topical application. The active agents of the present invention are generally administered topically, typically to the skin or mucous membrane of the patient. The formulation of the present invention is generally in the form of a pharmaceutical composition adapted to such a route, and in a dose effective for the treatment, prevention or mitigation intended.

The amount of therapeutically active compound that is administered and the dosage regimen for treating a condition with the compounds and/or compositions of this invention depends on a variety of factors, including the age, weight, sex and medical condition of the subject, the severity of the condition, the route and frequency of administration, and the particular compound employed, as well as the pharmacokinetic properties of the individual treated, and thus may vary widely. The dosage will generally be lower if the compounds are administered for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual.

The methods/uses of the present invention generally involve application of the formulation 1 to 5 times per day, typically 1 to 2 times per day, suitably one time per day.

The method of the present invention may be undertaken whenever required. Generally courses of treatment last 1 to 6 months depending on the nature and severity of the condition to be treated.

The formulation of the present invention is generally applied to a human.

In particular, there is provided a prophylactic method of preventing or minimizing the onset of the symptoms of a medical condition to a patient who has previously suffered from these symptoms.

Where the method of the present invention is used preventatively, a course of treatment may last up to six months. However, where the method is used to treat severe symptoms, the method/use may involve an initial strong dose of the active compound(s). This may be followed by a relatively lower dose for a second prolonged period of from, for instance 1 to 6 months.

The total amount of the formulation applied per dose is generally around 2.5-10.00 mg of formulation per $cm^2$ of skin treated.

The active compounds may be administered simultaneously, sequentially or separately. The active compounds may be provided as a combination package. The combination package may contain the product of the invention together with instructions for simultaneous, separate or sequential administration of each of the active compounds. For sequential administration, the active agents can be administered in any order.

The active compounds of the methods/uses of the invention may be provided as pharmaceutical compositions additionally containing one or more pharmaceutically acceptable diluents, excipients and/or carriers. This applies to both fixed and free combinations.

The phrase "pharmaceutically acceptable" is employed herein to refer to those compounds, materials, and/or compositions which are, within the scope of sound medical judgment, suitable for use in contact with the tissues of human beings or, as the case may be, an animal without excessive toxicity, irritation, allergic response, or other problem or complication, commensurate with a reasonable benefit/risk ratio. Such carriers are well known in the art and include buffers, fillers, extenders, binding agents, moisturizing agents, disintegrating agents, resorption accelerators, surface active agents, adsorptive carriers, lubricants and preservatives.

The patient is generally a human although in some embodiments, an animal may be treated.

Kit of Parts

According to a further aspect of the present invention, there is provided a kit of parts for use in the prevention, alleviation or treatment of a medical condition of the human or animal body, said kit of parts including the formulation described herein and an applicator device such as a syringe, spatula, or spray device.

The kit of parts may comprise the active compound(s) in dosage units containing a particular amount of the active compound. The dosage units may comprise one or more of the active compounds.

Generally the kit includes instructions for use, for example the nature of administration.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps. All documents referred to herein are incorporated by reference.

Specific Compositions

According to an embodiment of the present invention, there is provided a formulation for topical application comprising:

a. an active compound
b. a partition coefficient enhancer, in particular propylene glycol, butylene glycol, pentylene glycol, or hexylene glycol (generally propylene glycol),
c. a diffusion coefficient enhancer selected from the group consisting of a $C_{12}$ to $C_{14}$ saturated fatty acid and a $C_{14}$ saturated primary alcohol,
d. a hydrocarbyl methyl siloxane emollient selected from the group consisting of alkyl methyl siloxane compound or an alkyl aryl methyl siloxane compound and having a number average molecular weight of less than 500,
e. a dimethicone macromer surfactant, generally having a number average molecular weight of more than 1000, typically one or more selected from the group consisting of a macromer comprising a polyalkylsiloxane portion and one or more copolymers of ethylene oxide and propylene oxide or ionic pendant groups, and a pyrrolidone carboxylic acid functionalized dimethicone macromer,
f. a methyl siloxane, in particular a cyclomethicone compound having a number average molecular weight of less than 500, g. a cross-linked dimethicone macromer generally having a number average molecular weight of more than 1000, and generally comprising a polyalkylsiloxane portion.

An exemplary formulation of the present invention comprises:
i. 0.001% to about 10% w/w active compound
ii. 20 to 70% w/w propylene glycol, butylenes glycol, pentylene glycol, or hexylene glycol (generally propylene glycol)
iii. 0.5 to 5% w/w diffusion coefficient enhancer selected from the group consisting of a $C_{12}$ to $C_{14}$ saturated straight chain fatty acid and a $C_{14}$ saturated straight chain primary alcohol,
iv. 10 to 25% w/w hydrocarbyl methyl siloxane emollient comprising a mixture of an alkyl aryl methylsiloxane compound having a number average molecular weight of less than 500, a cross-linked dimethicone macromer generally having a number average molecular weight of more than 1000 typically one or more selected from the group consisting of a macromer comprising a polyalkylsiloxane portion and one or more copolymers of ethylene oxide and propylene oxide or ionic pendant groups, and a pyrrolidone carboxylic acid functionalized dimethicone macromer, wherein the mixture includes 10 to 20% w/w dimethicone macromer,
v. 10 to 25% w/w alkyl siloxane emollient comprising a mixture of cyclomethicone compound having a number average molecular weight of less than 500 and a cross-linked dimethicone macromer having a number average molecular weight of more than 1000, comprising a polyalkylsiloxane portion wherein the mixture includes 10 to 20% w/w silicone macromer.

The present invention will now be described by way of example only with reference to the accompanying figures and tables in which:

FIG. 10A shows the appearance after addition of the two dimethicone macromers, FIG. 10B shows the appearance after mixing, and FIG. 10C shows the appearance after addition of volatile hexamethyldisiloxane and final mixing.

FIG. 11 shows Table 1, formulations #1-10, according to the examples.

FIG. 12 shows Table 2, formulations #11-13, according to the examples.

FIG. 13 shows Table 3, formulations #14-16a, according to the examples.

FIG. 14 shows Table 4, formulations #17-20, according to the examples.

FIG. 15 shows Table 5, formulations #21-26, according to the examples. and

FIG. 16 shows Table 6, water-ethanol containing formulations #1-6, according to the examples.

Figure 1:
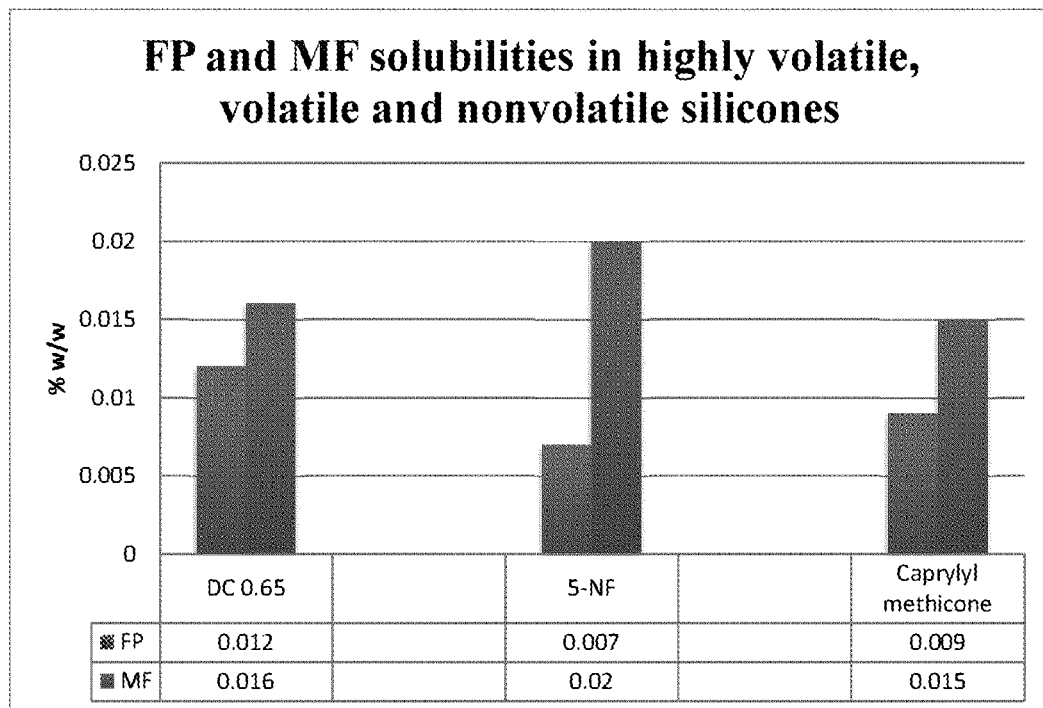
FIG. 1 shows the low saturated solubility of actives FP and MP in high volatile, volatile, and nonvolatile silicone compounds.
Figure 2:
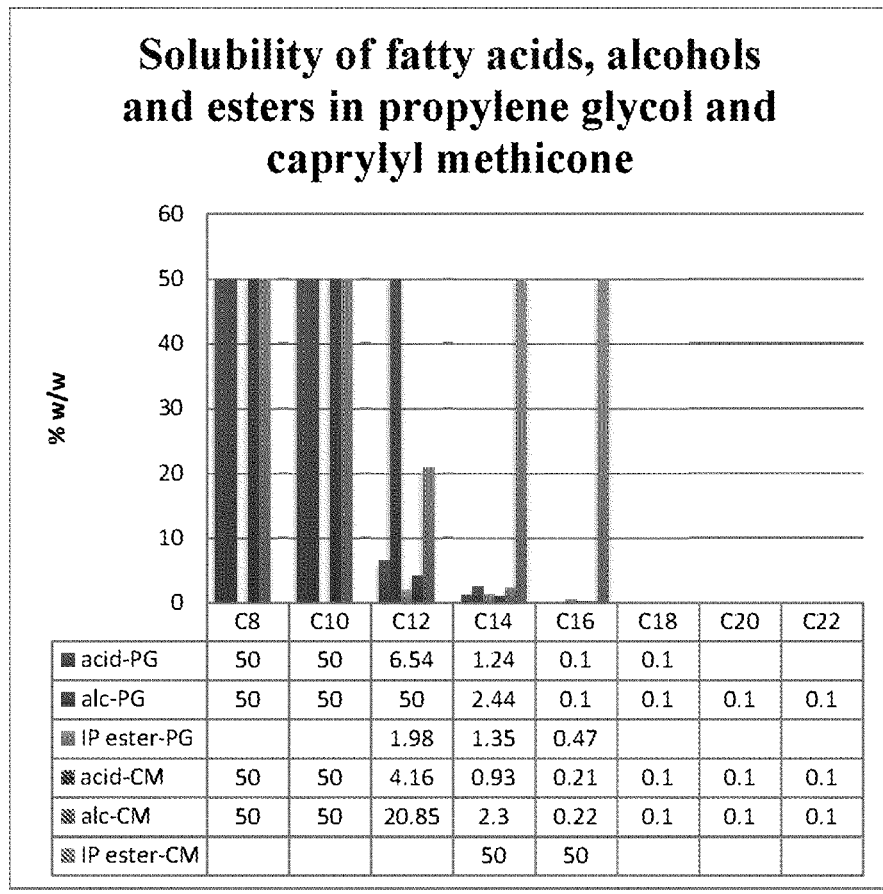
FIG. 2 shows the solubility of fatty acids, alcohols, and isopropyl esters of varying carbon chain length in propylene glycol and caprylyl methicone at 23-25° C.
Figure 3:
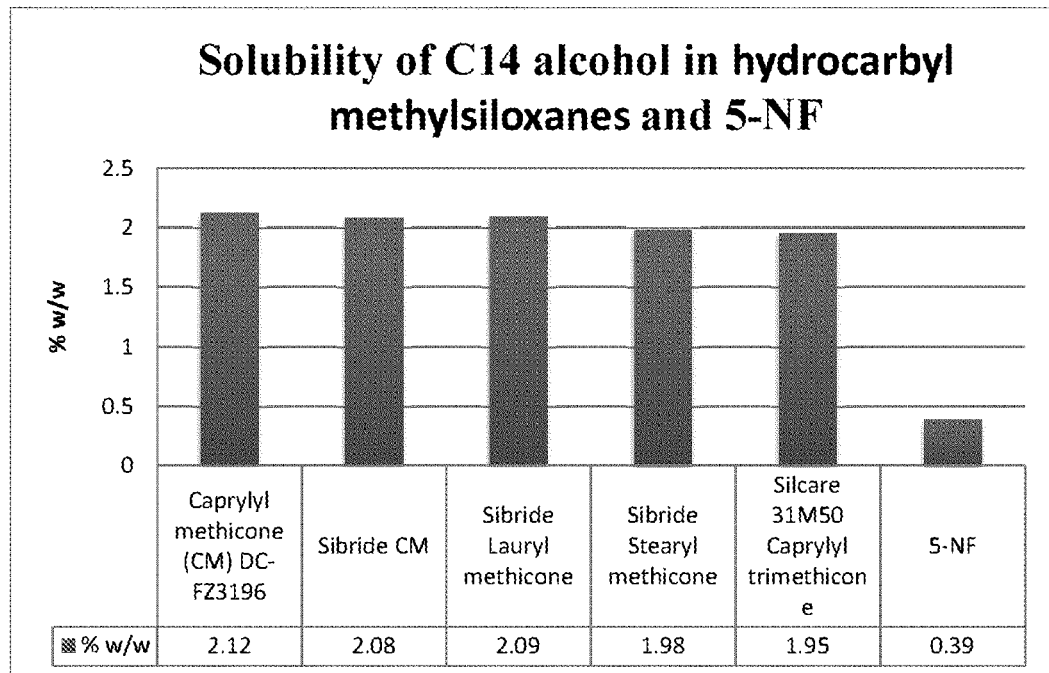
FIG. 3 shows that the saturated solubility of $C_{14}$ alcohol (myrystyl alcohol) at 23-25° C. across a range of liquid alkyl silicones including caprylyl methicone (Silbride CM), lauryl methicone (Silbride Lauryl methicone), stearyl methicone (Silbride stearyl methicone), caprylyl trimethicone (Silcare 31M50 Caprylyl trimethicone) and decamethylcyclopentasiloxane (5-NF).
Figure 4:
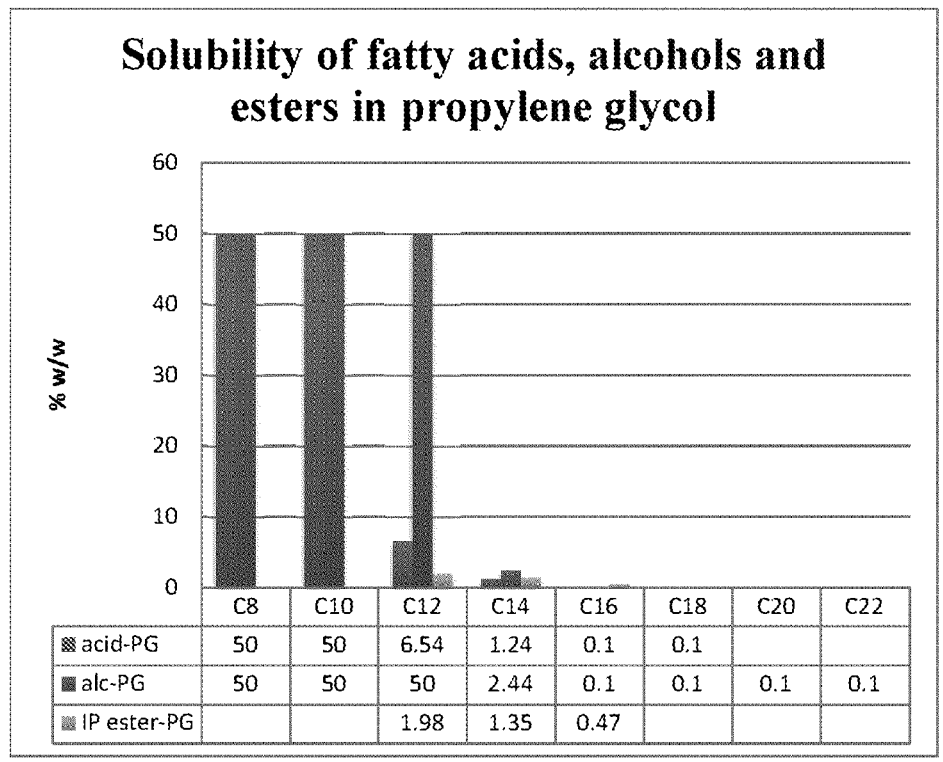
FIG. 4 shows the solubility of $C_8$-$C_{22}$ fatty acids, alcohols, and esters in propylene glycol at 23-25° C.
Figure 5:
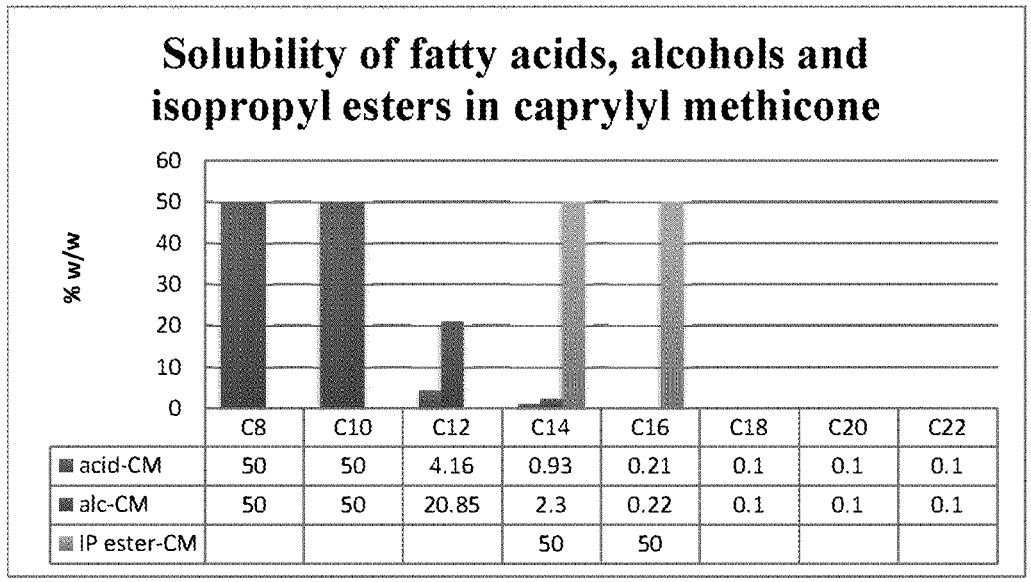
FIG. 5 shows the solubility of fatty acids, alcohols, and isopropyl esters in caprylyl methicone and propylene glycol at 23-25° C.
Figure 6:
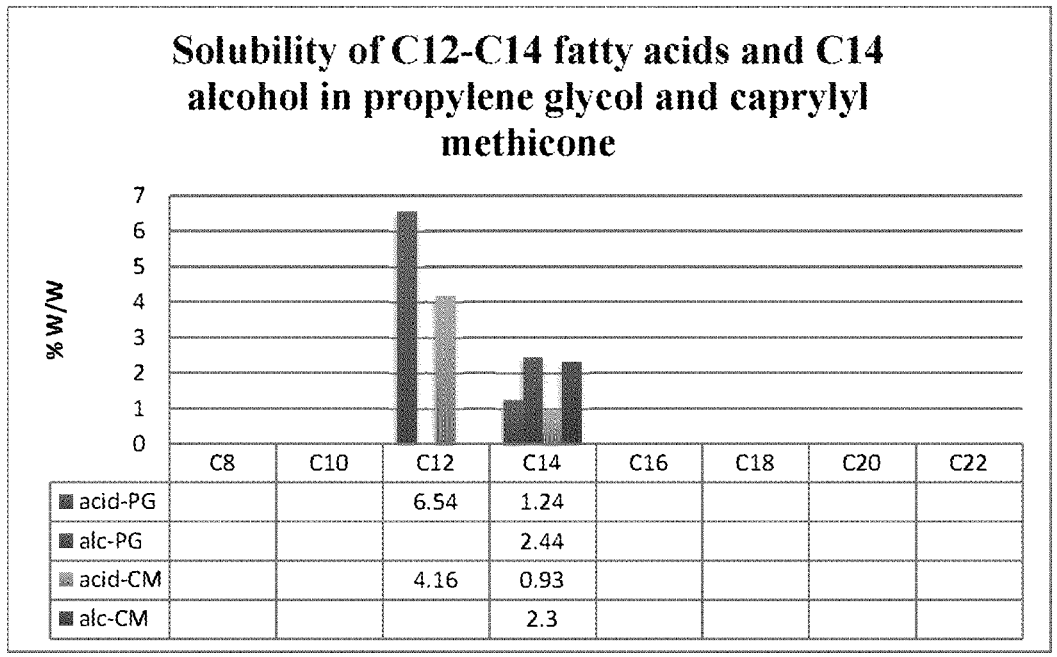
FIG. 6 shows the solubility of $C_{12}$-$C_{14}$ fatty acids and $C_{14}$ alcohol in propylene glycol and caprylyl methicone where the total solubility in both solvents does not exceed approximately 10% w/w.
Figure 7:
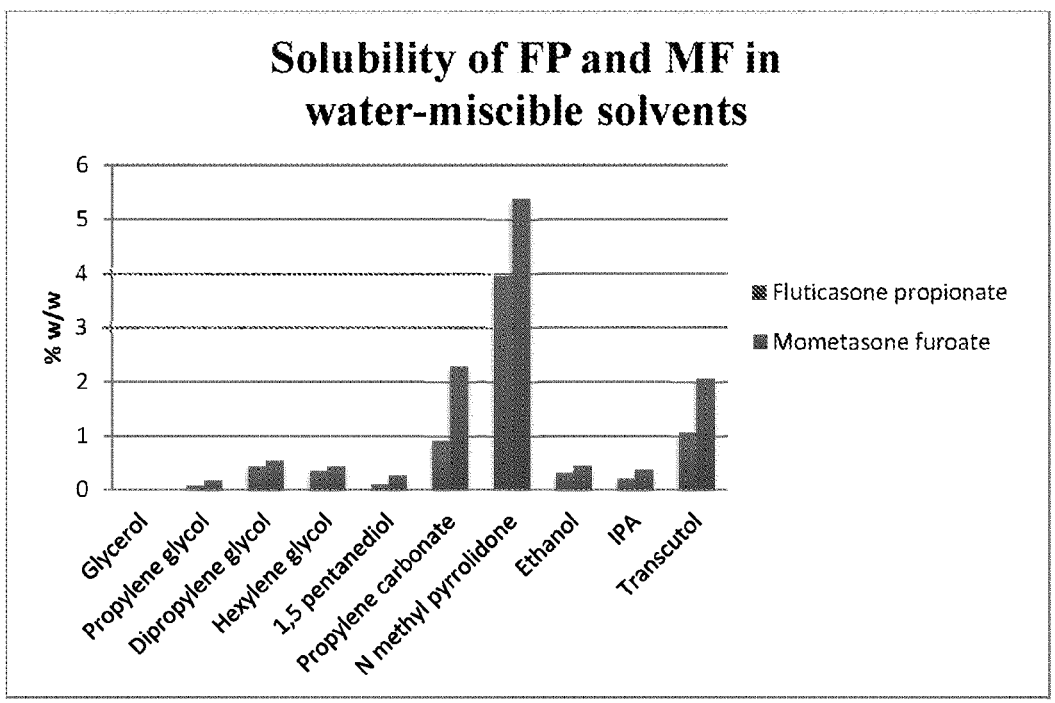
FIG. 7 shows the saturated solubility of actives FP and MP in various water-miscible solvents.
Figure 8:
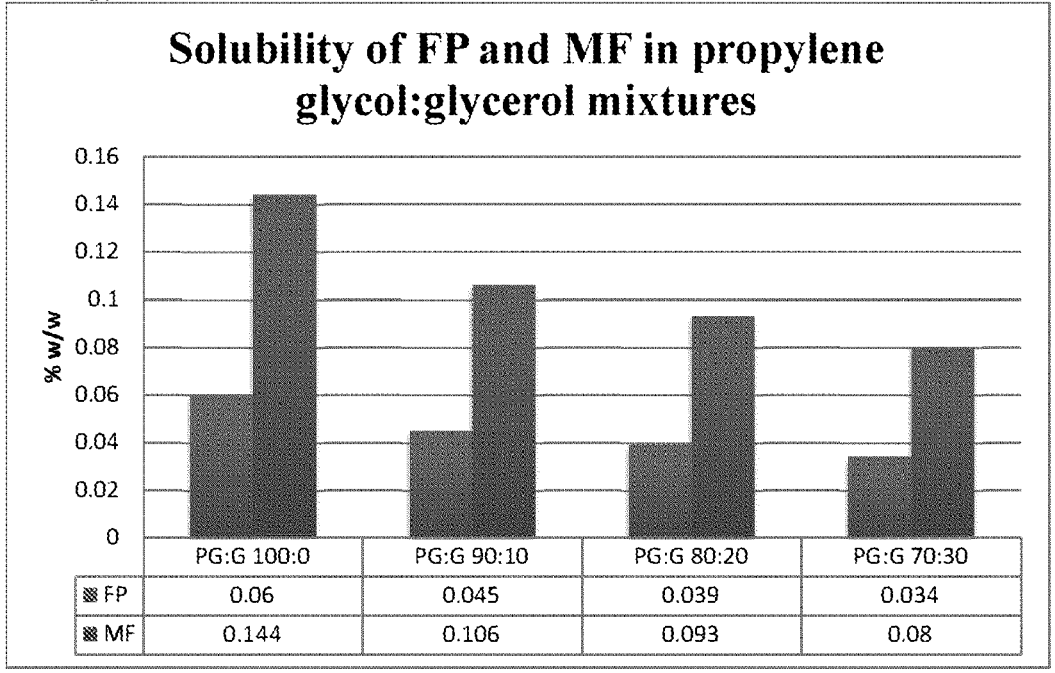
FIG. 8 shows the saturated solubility of actives FP and MP in propylene glycol:glycerol mixtures.
Figure 9:
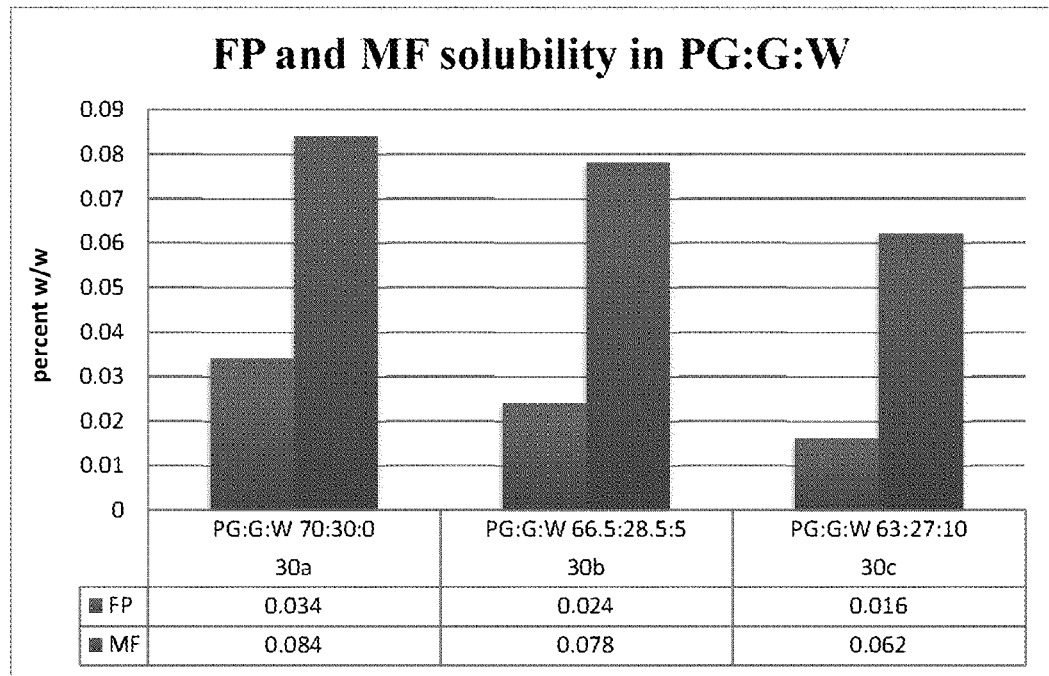
FIG. 9 shows the saturated solubility of actives FP and MP in propylene glycol:glycerol-water mixtures.
Figure 10A:
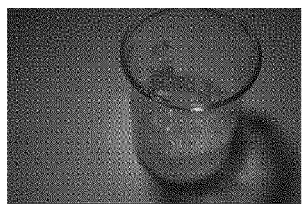
FIGS. 10A-10C shows the appearance of a composition comprising two dimethicone macromers.
Figure 10B:
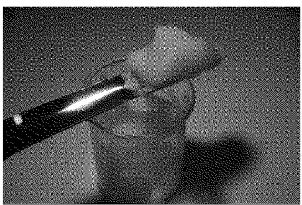
Figure 10C:
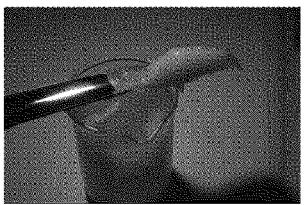

All of these formulations contain a nonvolatile residual phase as previously defined comprising:
a PC enhancer chosen from the diol series $C_nH_{n+2}O_2$ where n=3-6, or Transcutol P;
excepting Table #1 formulation #1, a DC enhancer chosen from the straight chain $C_{12}$-$C_{14}$ acids or $C_{14}$ alcohol series;
excepting Table #5 formulation #25, a hydrocarbylmethylsiloxane, namely caprlyl methicone, the elastomer dispersion silicone contained in EL-7040;
a volatile silicone oil, namely 5-NF the elastomer dispersion silicone contained in ST-Elastomer 10;
optionally, (Table #1 formulations #7-10) a nonvolatile silicone oil;
a dimethicone polyol or a dimethicone polyol elastomer emulsifier or ionic dimethicone emulsifier;
a cross-linked polyalkylsiloxane elastomer.

All of these formulations contain a highly volatile solvent as previously defined comprising:
in Tables #1-5, excepting Table #5 formulation #24, the highly volatile silicone DC 0.65, hexamethyldisiloxane;
in Table #6, only the highly volatile solvents ethanol and water are used.

The exemplified formulations are produced in accordance with the outline processes provided above.

On application to the skin as a thin film, evaporation of the highly volatile solvents quickly reforms the essential physicochemistry of the nonvolatile residual phase.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

1. Sabaté E, Adherence to Long-Term Therapies: Evidence for Action. (2003).
2. Cohen, A. D., Dreiher, J., Vardy, D. A. & Weitzman, D. Nonattendance in a dermatology clinic—a large sample analysis. *Journal of the European Academy of Dermatology and Venereology: JEADV* 22, 1178-1183 (2008).
3. Storm, A., Andersen, S. E., Benfeldt, E. & Serup, J. One in 3 prescriptions are never redeemed: primary nonadherence in an outpatient clinic. *Journal of the American Academy of Dermatology* 59, 27-33 (2008).
4. Carroll, C. L., Feldman, S. R., Camacho, F. T., Manuel, J. C. & Balkrishnan, R. Adherence to topical therapy decreases during the course of an 8-week psoriasis clinical trial: commonly used methods of measuring adherence to topical therapy overestimate actual use. *Journal of the American Academy of Dermatology* 51, 212-216 (2004).
5. Davis, S. A. & Feldman, S. R. Using Hawthorne effects to improve adherence in clinical practice: lessons from clinical trials. *JAMA dermatology* 149, 490-491 (2013).
6. Krejci-Manwaring, J., et al. Stealth monitoring of adherence to topical medication: adherence is very poor in children with atopic dermatitis. *Journal of the American Academy of Dermatology* 56, 211-216 (2007).
7. Feldman, S. R. & Yentzer, B. A. Topical clobetasol propionate in the treatment of psoriasis: a review of newer formulations. *American journal of clinical dermatology* 10, 397-406 (2009).
8. Krejci-Manwaring, J., et al. Adherence with topical treatment is poor compared with adherence with oral agents: implications for effective clinical use of topical agents. *Journal of the American Academy of Dermatology* 54, S235-236 (2006).
9. Zschocke, I., Mrowietz, U., Karakasili, E. & Reich, K. Non-adherence and measures to improve adherence in the topical treatment of psoriasis. *Journal of the European Academy of Dermatology and Venereology: JEADV* 28 Suppl 2, 4-9 (2014).
10. Tan, X., Feldman, S. R., Chang, J. & Balkrishnan, R. Topical drug delivery systems in dermatology: a review of patient adherence issues. *Expert opinion on drug delivery* 9, 1263-1271 (2012).
11. Devaux, S., et al. Adherence to topical treatment in psoriasis: a systematic literature review. *Journal of the European Academy of Dermatology and Venereology: JEADV* 26 Suppl 3, 61-67 (2012).
12. Warino, L., Balkrishnan, R. & Feldman, S. R. Clobetasol propionate for psoriasis: are ointments really more potent? *Journal of drugs in dermatology: JDD* 5, 527-532 (2006).
13. Lehman, P. A. & Franz, T. J. Assessing topical bioavailability and bioequivalence: a comparison of the in vitro permeation test and the vasoconstrictor assay. *Pharmaceutical research* 31, 3529-3537 (2014).

The invention claimed is:
1. A formulation for topical application comprising:
   a non-volatile residual phase comprising:
      an active compound,
      10 to 60% w/w of a partition coefficient enhancer (PC enhancer), having a structure of the general formula: $CnH_{2n+2}O_2$ where n represents an integer from 3 to 6 inclusive,
      about 0.5 to about 10% w/w of a diffusion coefficient enhancer (DC enhancer) selected from the group consisting of a $C_{12}$ to $C_{14}$ straight chain fatty acid and a $C_{14}$ straight chain primary alcohol, and
   an emollient phase comprising:
      5 to 45% w/w of a first dimethicone macromer mixture including a dimethicone macromer and a hydrocarbyl methyl siloxane emollient selected from the group consisting of an alkyl methyl siloxane, an aryl methyl siloxane and an alkyl aryl methyl siloxane, and
      5 to 45% w/w of a second dimethicone macromer mixture including a methyl siloxane compound and a cross-linked dimethicone macromer.
2. The formulation of claim 1, wherein the first dimethicone macromer mixture includes a polyglycol dimethicone macromer.

3. The formulation of claim 1, wherein the first dimethicone macromer mixture includes a compound of the following structure:

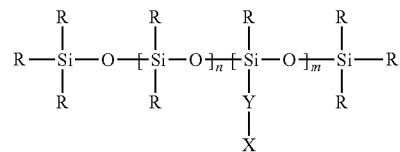

where,
R represents H or a C1 to C6 alkyl hydrocarbyl group;
Y represents a C1 to C6 alkyl hydrocarbyl group;
X represents an amine, a quaternary amino group, or acid functionality; and
m and n independently represent an integer from 1 to 50.
4. The formulation of claim 1, wherein the first dimethicone macromer mixture includes a dimethicone macromer having a number average molecular weight of more than 1000, and a hydrocarbyl methyl siloxane emollient having a number average molecular weight of less than 500.
5. The formulation of claim 1, wherein the first dimethicone macromer mixture includes a polyglycol dimethicone macromer cross-linked with a polyalkylene oxide compound or cross-linked with a diene.
6. The formulation of claim 5, wherein the first dimethicone macromer mixture includes a polyglycol dimethicone macromer selected from the group consisting of polyethylene glycol (PEG) dimethicone, polypropylene glycol (PPG) crosspolymer, and PEG dimethicone bis-isoalkyl PPG crosspolymer.
7. The formulation of claim 1, wherein the first dimethicone macromer mixture includes a polyglycol dimethicone macromer comprising one or more pendant groups from the dimethicone backbone, wherein said pendant groups comprise a polyalkylene oxide group.
8. The formulation of claim 7, wherein the polyglycol dimethicone macromer includes a polyethylene glycol pendant group and a polypropylene glycol pendant group from the dimethicone backbone.
9. The formulation of claim 1, comprising 10 to 40% w/w of the first dimethicone macromer mixture.
10. The formulation of claim 1, wherein the second dimethicone macromer mixture includes a methyl siloxane compound having a number average molecular weight of less than 1000, and a cross-linked polyalkylsiloxane diol dimethicone macromer having a number average molecular weight of more than 1000.
11. The formulation of claim 10, wherein the methyl siloxane compound comprises decamethylcyclopentasiloxane.
12. The formulation of claim 1, wherein the formulation comprises 10 to 40% w/w of the second dimethicone macromer mixture.
13. The formulation of claim 1, wherein the first dimethicone macromer mixture comprises 5 to 30% w/w polyglycol dimethicone macromer.
14. The formulation of claim 1, wherein the second dimethicone macromer mixture comprises 5 to 30% w/w cross-linked dimethicone macromer.
15. The formulation of claim 1, wherein the PC enhancer is selected from one or more of the group consisting of propylene glycol, butylene glycol, pentylene glycol and hexylene glycol.

16. The formulation of claim 15, wherein the formulation further comprises a second mutually miscible PC enhancer/cosolvent selected from the group consisting of an alcohol, ether-alcohol, diol, triol, and alkyl pyrrolidone.

17. The formulation of claim 16, wherein the second mutually miscible PC enhancer/cosolvent is selected from the group consisting of a diol of the general formula $CnH_{2n+2}O_2$, where n represents an integer greater than 6; an alcohol of the general formula $CnH_{2n+2}O$, where n represents an integer 2 or 3; and an ether-alcohol of the general formula $CnH_{2n+2}O_3$ or $CnH_{2n+2}O_2$, where n represents an integer from 1 to 10 or an alkyl pyrrolidone.

18. The formulation of claim 17, wherein the second mutually miscible PC enhancer/cosolvent is glycerol or N-methyl pyrrolidone.

19. The formulation of claim 1, wherein the formulation comprises 25 to 45% w/w PC enhancer.

20. The formulation of claim 1, wherein the formulation comprises less than about 5% w/w of the diffusion coefficient enhancer.

21. The formulation of claim 1, wherein the formulation further comprises a highly volatile solvent selected from the group consisting of hexamethyldisiloxane, octamethyltrisiloxane, ethanol, isopropyl alcohol, and water.

22. The formulation of claim 1, wherein the active compound is selected from the group consisting of retinoids, retinoic acid metabolic blocking agents (RAMBAs), alpha and beta hydroxy acids and polymers and derivatives thereof, immune response modifier compounds, vitamin D analogues, corticosteroids, anti-rosacea agents, antihistamines, antibacterial agents, antiacne agents, antifungal agents, antiviral agents, cytotoxic agents, psoralens, anti-alopecia agents, anti-androgens, anti-pruritic agents, keratolytic agents, skin lightening and depigmenting agents, dithranol, antiseptics, anaesthetics, analgesic, neuropathic and non-steroidal anti-inflammatory agents, vasoactive agents and agents to combat dry and ageing skin.

23. The formulation of claim 1, wherein the alkyl methyl siloxane comprises caprylyl methicone, lauryl methicone, stearyl methicone, or caprylyl trimethicone.

24. The formulation of claim 1, wherein the DC enhancer is selected from the group consisting of lauric acid, myristic acid, and myristyl alcohol.

25. A kit of parts for use in the prevention, alleviation or treatment of a medical condition of the human or animal body, said kit of parts including the formulation of claim 1 and an applicator device selected from a syringe, spatula, or spray device.

26. A method of preventing, reducing the likelihood of, alleviating or treating a medical condition in or of the human or animal body comprising:
topically administering a therapeutically effective amount of the formulation of claim 1,
wherein the medical condition is caused by or associated with one or more of pain and/or inflammation, pruritus, acne, eczema, psoriasis, nappy rash, rosacea, dry skin, microbial conditions, ageing skin, alopecia, and hypoandrogenism.

27. The method of claim 26, wherein the formulation is applied to the skin or mucous membrane(s) of the human or animal body.

28. The formulation of claim 1, wherein the formulation comprises 10% w/w or less of water.

29. The formulation of claim 1, wherein the formulation does not comprise water.

* * * * *